US006776896B1

(12) United States Patent  
Osipchuk

(10) Patent No.: US 6,776,896 B1
(45) Date of Patent: Aug. 17, 2004

(54) METHOD OF POSITIONING CELLS FOR ELECTROPHYSIOLOGICAL TESTING

(75) Inventor: Yuri Osipchuk, Foster City, CA (US)

(73) Assignee: Axon Instruments, Inc., Union City, CA (US)

( * ) Notice: Subject to any disclaimer, the term of this patent is extended or adjusted under 35 U.S.C. 154(b) by 118 days.

(21) Appl. No.: 09/973,388

(22) Filed: Oct. 9, 2001

Related U.S. Application Data

(60) Provisional application No. 60/239,697, filed on Oct. 11, 2000.
(51) Int. Cl.[7] .............................................. G01N 27/327
(52) U.S. Cl. ............................. 205/777.5; 204/403.01; 435/7.21; 435/173.4
(58) Field of Search .......................... 205/777.5, 778; 24/403.01; 435/7.21, 173.4, 287.3

(56) References Cited

U.S. PATENT DOCUMENTS

| 6,300,108 B1 | * | 10/2001 | Rubinsky et al. ........ 435/173.6 |
| 6,368,851 B1 | * | 4/2002 | Baumann et al. ........ 435/285.2 |
| 2002/0064841 A1 | * | 5/2002 | Klemic et al. .............. 435/164 |

FOREIGN PATENT DOCUMENTS

| WO | WO 01/25769 A2 | * | 4/2001 |
| WO | WO 01/27614 A1 | | 4/2001 |
| WO | WO 01/48474 A1 | | 7/2001 |

OTHER PUBLICATIONS

Kostyuk et al, Nature, vol. 257, pp. 691–693, 1975.*

Cover page of WO 99/31503, Jun. 24, 1999.

* cited by examiner

*Primary Examiner*—Kaj K. Olsen
(74) *Attorney, Agent, or Firm*—Antonio R. Durando; Quarles & Brady Streich Lang LLP

(57) ABSTRACT

A perfusion-chamber structure includes a chamber plate with an extracellular compartment, a partition plate with an electrode aperture, and a foundation plate with an intracellular compartment. A gap between the chamber plate and the partition plate produces a channel for applying suction that draws extracellular solution from the extracellular compartment and facilitates the movement and positioning of a test cell over the electrode aperture. The positioning procedure for the test cell is accompanied by a slight positive pressure applied to the intracellular solution in the intracellular compartment of the perfusion chamber to cause upward fluid flow through the electrode aperture. When the cell is positioned over the electrode aperture, the positive pressure on the intracellular fluid is reversed to suction and the cell is seated thereby to form the seal.

24 Claims, 18 Drawing Sheets

METHOD OF POSITIONING CELLS FOR ELECTROPHYSIOLOGICAL TESTING

RELATED APPLICATIONS

This application is based on U.S. Provisional Application Serial No. 60/239,697, filed on Oct. 11, 2000.

BACKGROUND OF THE INVENTION

1. Field of the Invention

This invention is related in general to electrodes for electrophysiological testing of biological membranes. In particular, the invention concerns the manufacture of an electrode assembly suitable for massive parallel electrophysiological testing of cells, and a method for rapidly and reliably positioning the cells in each chamber for forming a high electrical-resistance patch clamp.

2. Description of the Related Art

In conventional voltage-clamping techniques used to conduct electrophysiological tests on a membrane, the electrical activity in the membrane is assessed by measuring current or voltage changes produced in response to exposure to various test stimuli. Typically, the membrane is pierced with two microelectrodes connected to an amplifier capable of recording current or voltage variations in response to stimuli such as voltage step changes, current injection, the application of compounds, or mechanical stimulation.

Similarly, using patch-clamping techniques, the membrane potential can be held constant while the current flowing through the membrane is measured to detect ion-channel activity that corresponds to changes in the membrane's conductance. Instead of using sharp microelectrodes to puncture the membrane and penetrate the cell, like in traditional voltage clamping, patch clamping uses a micropipette with a heat-polished tip of about 1 to 5 $\mu$m in diameter that is physically sealed to a "patch" on the membrane. The same pipette is used continuously for both current passing and voltage recording.

For the most part, patch clamping is used either in a whole-cell or a single-channel mode of operation. In whole-cell patch clamping, the membrane at the tip of the pipette is ruptured to produce electrical continuity between the electrolyte in the pipette and the interior of the cell. Thus, total membrane current or voltage is measured. In single-channel patch clamping, the integrity of the membrane at the tip of the pipette is preserved. Accordingly, the recorded current is only the current flowing through the patch of the membrane enclosed by the tip of the pipette. Since this area is very small, there is a good chance that only one or a small number of ion channels may be in the membrane patch, and individual ion-channel currents may be recorded.

In both types of patch-clamp techniques, when the tip of the pipette is pressed against the cell membrane, the interior of the pipette is isolated from the extracellular solution by the seal that is formed between the tip of the pipette and the membrane. If the electrical resistance of the seal is very high (in the order of several hundred mega-ohm to one giga-ohm), no current can leak across the seal and good measurements are obtained. Thus, any leakage of current through the seal is undesirable and the creation of a high-resistance seal (in the order of giga-ohms) is crucial for good results.

New patch-clamp electrodes have recently been developed in the art based on a seal formed by a test cell's membrane and an aperture in a nonconductive partition separating the extracellular carrier solution from an intracellular electrolyte. The plate configuration of the partition allows the manufacture of trays with multiple perfusion chambers for parallel testing of large numbers of cells. Accordingly, new insulating seal materials and patch-clamp seal geometries are being investigated in the art to improve the quality of the seals and the speed of testing in such parallel operations. Typically, these new systems comprise multiple perfusion chambers where the partition separates an upper (extracellular) compartment, where the test cells are suspended in an extracellular solution toward the aperture for forming a patch-clamp seal with it, from a bottom (intracellular) compartment containing an electrode and an electrolytic solution. For instance, Cytion's International Application No. PCT/IB98/01150 describes a perforated partition with multiple holes to form a plurality of patch-clamp seals between intra and extracellular compartments. In International Application No. PCT/EP00/08895, a system is described where a pulsatile negative pressure is used to position the test cell on a perforated surface in a high-resistance seal arrangement. The suction is also used to penetrate the membrane of the cell and connect its interior to the ambient electrolytic solution. Similarly, International Application No. PCT/GB00/04887 discloses a system where a test cell is drawn to form a seal in an aperture in a well by suction through the well and through lateral channels that increase fluid flow in the desired direction. These channels are also used to remove the cell by reversing the direction of flow.

In addition to the ability to form a high-resistance seal, good electrophysiological testing requires that each cell be placed on the electrode aperture without excessive mixing (optimally with no mixing) of extracellular solution (contained in the upper extracellular compartment) with the intracellular electrolytic solution contained in the lower intracellular compartment. When such mixing occurs, the homogeneity of the intracellular solution is reduced and its function is adversely affected for proper recording of electrophysiological responses. Therefore, systems that apply suction to place the test cells on the electrode apertures are subject to erroneous measurements that detrimentally affect their performance. This invention provides a different approach to solve this problem.

BRIEF SUMMARY OF THE INVENTION

An important objective of this invention is a method of positioning a cell or other biological membrane on an electrode aperture rapidly and with minimal mixing of extracellular and intracellular solutions to form a high-resistance seal.

Another object is a positioning procedure and apparatus that afford a high degree of control over the flow of the extracellular solution and the intracellular solution in the system.

Still another objective of the invention is a high-resistance electrode assembly suitable for the parallel testing of large numbers of biological membranes, such as animal cells, through successive exposures to multiple perfusion solutions in a continuous, high-throughput operation.

Another goal is an electrode assembly design that is suitable for implementation within an overall automated high-resistance patch-clamp and solution-delivery system.

Another objective is a modular method of manufacture of the electrode assembly, such that each component may be fabricated independently with known techniques and combined to implement the precise structural details required for the electrical and fluidic systems of electrophysiological perfusion chambers.

Yet another object is a system that can be implemented using conventional patch-clamp electronic hardware and software, modified only to the extent necessary to meet the design parameters of the electrode assembly of the invention.

A final objective is a system that can be implemented economically according to the above stated criteria.

Therefore, according to these and other objectives, the present invention consists of a perfusion-chamber structure that includes a chamber plate with an extracellular compartment, a partition plate with an electrode aperture, and a foundation plate with an intracellular compartment. A gap between the chamber plate and the partition plate produces a channel for applying suction that draws extracellular solution from the extracellular compartment and facilitates the movement and positioning of a test cell over the electrode aperture. According to a very important aspect of the invention, the suction portion of the positioning procedure for the test cell is accompanied by a slight positive pressure applied to the intracellular solution in the intracellular compartment of the chamber to cause upward flow of the intracellular solution through the electrode aperture. As a result of the concurrent suction and pressure flows produced in the vicinity of the electrode aperture, the test cell is separated from impurities that may be present in the extracellular solution, thereby permitting a clean contact with the electrode aperture and correspondingly the formation of a high-resistance seal. Because of the upward flow of intracellular solution through the electrode aperture, the intracellular compartment of the chamber is not contaminated with extracellular solution, thereby avoiding the detrimental effects experienced when only suction is used to draw the test cell to the electrode aperture. When the cell is positioned over the electrode aperture, the positive pressure on the intracellular fluid is reversed to suction and the cell is seated thereby to form the seal.

According to another aspect of the invention, an electrode assembly for parallel electrophysiological recording of large numbers of cells comprises multiple plate components suitable for combination and connection with conventional electronic and fluid transfer systems. In the preferred embodiment, the assembly includes a top disposable section and a bottom permanent section. The top section comprises a large number of perfusion chambers for parallel testing, each chamber having an upper funnel-like compartment and a lower tubular channel separated by an electrode aperture adapted to receive a cell from an extracellular carrier solution. The bottom section comprises mating electrical couplers and tubular flow ports aligned with corresponding metallic leads and channels in the upper section for connection to computer-controlled electronic and fluid-flow hardware. The two sections are combined for operation in a simple, clamped arrangement that ensures hermetic and insulated connection of the fluidic and electrical systems, respectively. The electrode assembly is made with various plate components that may be produced independently and combined to form the top and bottom sections. These plates may be manufactured with precise definition utilizing etching and other techniques known in the art of electronic-component fabrication.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

A major aspect of this invention lies in the procedure used to draw a biological membrane toward an electrode aperture to form a seal in a perfusion chamber for electrophysiological recording. A pressure (positive or negative) is applied to the extracellular fluid in the extracellular compartment of the chamber to cause flow of the biological membrane being tested toward the electrode aperture. At the same time, sufficient positive pressure is applied to the intracellular fluid in the intracellular compartment to either cause flow of intracellular fluid into the extracellular compartment through the electrode aperture or at least prevent flow of extracellular fluid into the intracellular compartment. When the biological membrane approaches the electrode aperture in the extracellular compartment, suction is applied to the aperture from the intracellular compartment to draw the membrane in and form a seal. The initial countercurrent flows of fluids near the electrode aperture in the extracellular compartment greatly improve the process of seating the biological membrane over the electrode aperture in the electrode to form a high-resistance electrical seal while minimizing detrimental mixing of intracellular and extracellular solutions.

The terms perfusion chamber and electrode are used interchangeably herein to refer to a structure that includes an electrode-aperture partition separated by an extracellular compartment with an extracellular fluid carrying a test cell and an intracellular compartment with an intracellular electrolyte connected to a metallic electrode. The terms extracellular solution and extracellular fluid are used to refer to the fluid in the extracellular compartment, also often referred to in the art as extracellular saline, external, and perfusion solution or fluid. Similarly, the terms intracellular solution and intracellular fluid are used to refer to the fluid in the intracellular compartment, also often referred to in the art as intracellular saline, internal, and electrolyte solution or fluid.

The terms suction and negative pressure are used interchangeably with reference to pressure applied at a given location to a body of fluid, channel or compartment to refer to a condition wherein said pressure is less than the pressure applied at some other location to the body of fluid, channel or compartment. Finally, the term funnel is intended to refer to any structure designed to direct fluid flow toward an exit orifice oriented in a particular direction. Accordingly, it is intended to encompass also structures without a converging flow path, such as tubular channels and the like.

The invention is described primarily with reference to cells, but it is understood that it applies to, and can be practiced in the same manner with, vesicles and other biological membranes. Therefore, the scope of the invention should not be limited to any particular test sample, so long as suitable for producing a patch-clamp seal as described herein.

Figure 1:
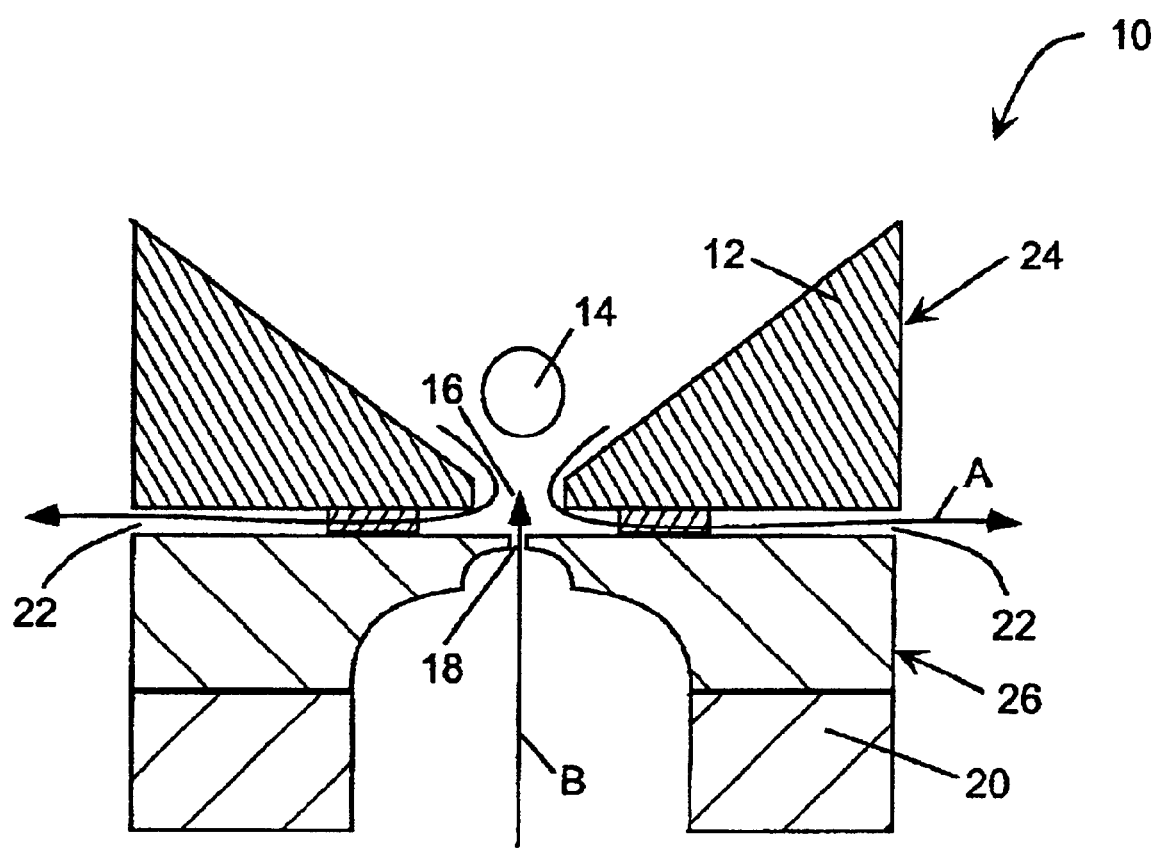
FIG. 1 is a schematic sectional representation of a perfusion chamber illustrating countercurrent flow of extracellular fluid and intracellular fluid, according to the present invention, during the process of positioning the test cell over the electrode aperture.

Referring to the figures, wherein the same reference numerals and symbols are used throughout for like parts, FIG. 1 is a schematic representation of a sectioned perfusion chamber 10 suitable to practice the cell-positioning procedure of the invention. The chamber includes an upper, funnel-like, extracellular compartment 12 where test cells 14 are carried by an extracellular solution and directed through a bottom opening 16 to form a high-resistance seal with an electrode aperture or hole 18 for electrophysiological recording. An intracellular solution is contained in a lower, tubular, intracellular compartment 20 to provide electrical conductivity between the patch and a metallic electrode (not shown). An open channel 22 for fluid flow around the top side of the electrode aperture 18 is provided by spacing the "partition" plate 24 containing the electrode aperture apart from the chamber 26 containing the extracellular compartment 12. Thus, fluid flow is possible in all directions through the funnel opening 16, the electrode aperture 18, and the channel 22.

According to the invention, the cell 14 is drawn toward and positioned over the electrode aperture 18 by the concurrent application of negative pressure to the channel 22, so that extracellular fluid is withdrawn from the extracellular compartment 12, and of positive pressure applied in the intracellular compartment 20 to push the intracellular electrolyte upward through the electrode aperture 18 to mix with extracellular fluid above the hole in the area of the funnel opening 16. As a result of this countercurrent flow of fluids, the motion of the cell 14 is promoted toward the electrode aperture 18 by the flow of extracellular fluid (illustrated by arrows A), but it is also slightly resisted by the upper flow of intracellular electrolyte (arrow B), which tends to remove any impurities present in the extracellular fluid in the vicinity of the cell membrane. Thus, a better contact between the cell 14 and the electrode aperture 18 is possible, which in turn produces an improved patch-clamp seal. At the same time, no extracellular fluid is allowed to mix with the intracellular fluid in the lower intracellular compartment 20, which eliminates measurement errors produced by the difference in composition and conductivity of the two solutions.

Figure 2:
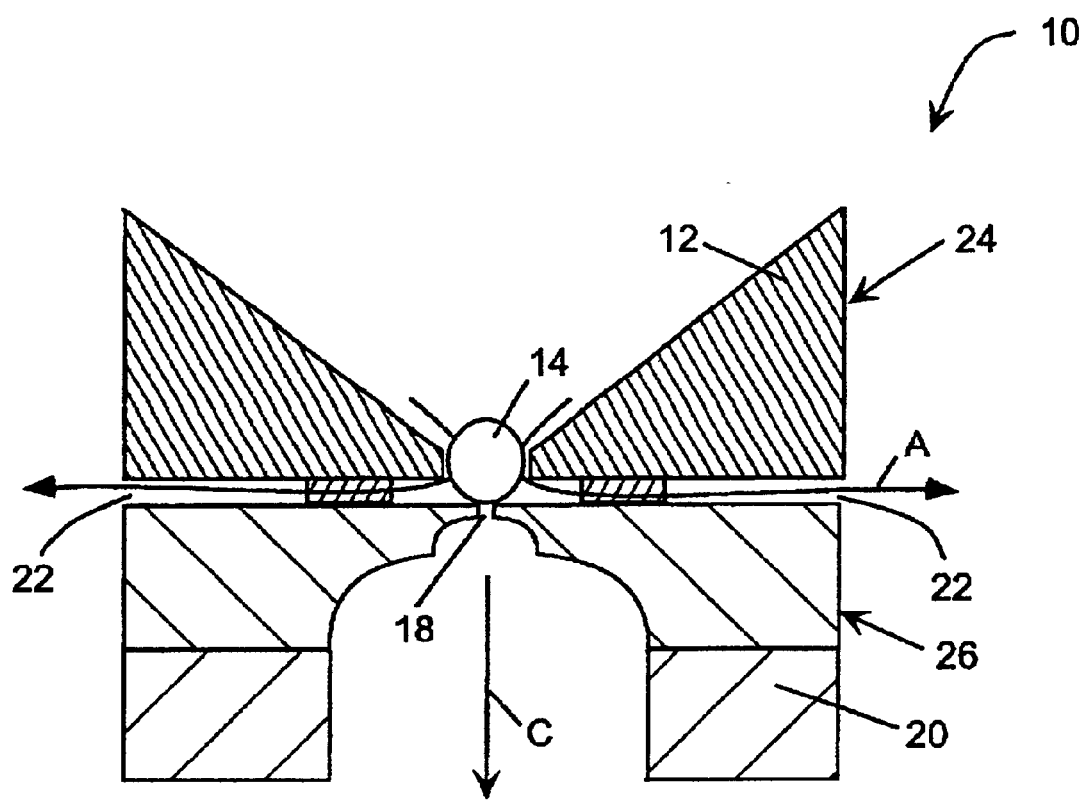
FIG. 2 is the diagram of FIG. 1 illustrating the reversed flow of intracellular fluid.

The position of the cell 14 relative to the electrode aperture 18 may be detected by monitoring changes in the electrical resistance across the hole by conventional means used in the art. Once the membrane of the cell 14 has contacted the rim of the electrode aperture 18, as illustrated in FIG. 2, the direction of flow of the intracellular solution is reversed by applying suction to the intracellular compartment 20, as indicated by arrow C. This causes the cell 14 to seat firmly on the electrode aperture 18, to form a high-resistance seal therewith, and, upon application of further, preferably pulsatile, suction, to rupture and expose the interior of the cell to the intracellular solution in the intracellular compartment 20. Thus, the patch-clamp seal is formed without any intrusion of extracellular fluid into the intracellular solution. At the same time, the intracellular fluid passed into the extracellular fluid through the electrode aperture 18 prior to forming a seal is mostly removed through the channels 22. To the extent that some intracellular fluid remains above the cell 14 after the seal is formed, the continuous flow of extracellular fluid disperses the intracellular fluid rapidly with no noticeable effect resulting from its presence.

As is well understood in the art, patch-clamp apertures such as the electrode apertures 18 have to be in the submicron to few-micron range in diameter in order to produce a useable patch-clamp seal for electrophysiological measurements. Accordingly, appropriate manufacturing techniques that provide control over the size, configuration and structural quality of the electrode apertures must be used. One such technique is by etching a substrate made of solid insulating material.

Various processes for etching solid insulating materials such as glass, silicon or polymers, as required to produce a workable patch-hole structure, are well known. Some etching techniques consist of isotropic processes, such as chemical wet etching; others are anisotropic (directional), such as etching by ion-beam milling. These methods are widely used in semiconductor chip fabrication and other applications.

Techniques for creating etching masks are also well known and widely used. One method consists of depositing a photoresist material on the surface of a substrate, photo-projecting an image of the pattern to be created onto the photoresist mask, and developing the photoresist. There are two types of photoresist materials, positive and negative. With a positive photoresist, the non-exposed areas of photoresist are removed during the development phase to create a mask; with a negative photoresist, the exposed areas are removed.

Figure 3:
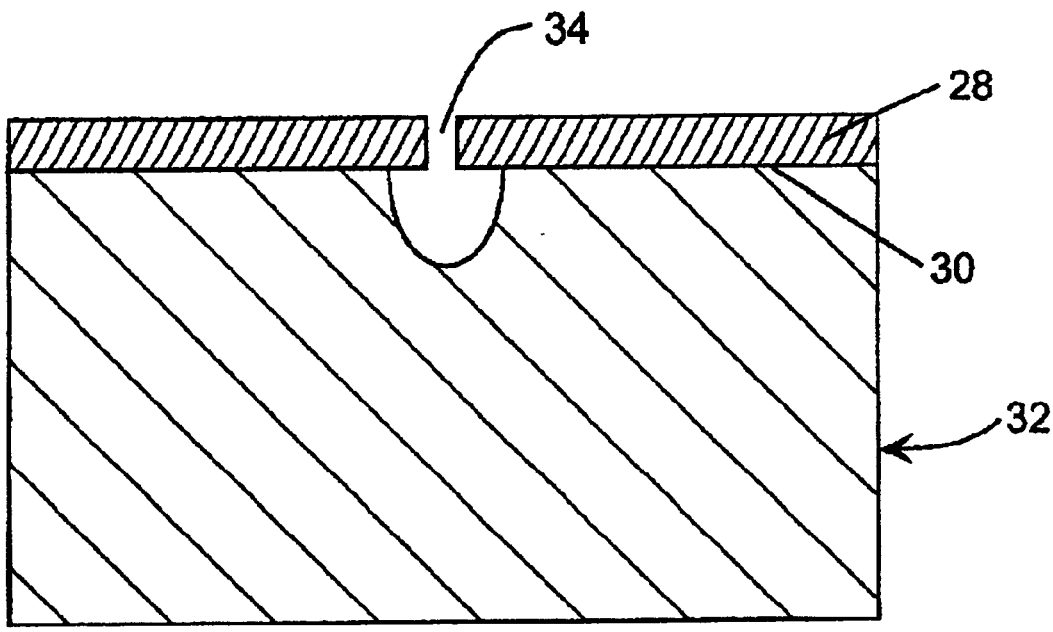
FIG. 3(a) is a schematic diagram illustrating etching of a substrate through a photoresist mask using an isotropic process.
FIG. 3(b) is a schematic diagram illustrating etching of a in substrate through a photoresist mask using an anisotropic process.
Figure 3:
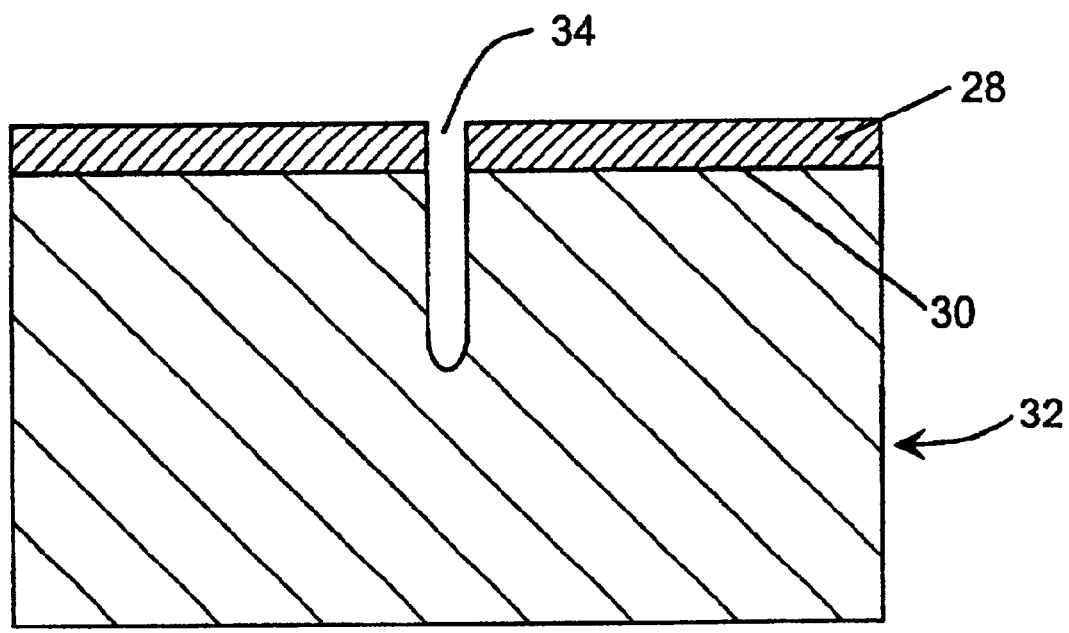

A partition plate with an array of electrode apertures may be fabricated through a series of etching steps from a thin sheet of substrate material (such as glass or some other suitable material). As illustrated in FIGS. 3(a) and (b) with respect to the formation of a single electrode aperture, a photoresist mask 28 is created on the top surface 30 of a substrate 32 with a number of openings 34 in the mask corresponding to the locations of the desired electrode apertures. The electrode apertures 18 are then etched through the sheet of substrate 32, by either isotropic or anisotropic etching, as shown in FIGS. 3(a) and (b), respectively. In the case of isotropic etching, a disadvantage of the approach is that the thickness of the substrate 32 has to be comparable with or smaller than approximately half the diameter of the electrode aperture produced by etching. For example, to create a 1-$\mu$m hole, the thickness of the substrate 32 has to be on the order of 0.5 $\mu$m. Thus, because thin sheets of material are very difficult to work with, isotropic etching is impractical for creating small through-holes in the substrate.

Anisotropic etching processes, such as by ion-milling or plasma etching, allow instead for creating patterns with substantially larger aspect ratios (that is, the ratio of the length of the hole produced by etching to its diameter), so that the starting thickness of the substrate 32 can be materially larger. Still, it is difficult to achieve aspect ratios larger than about 10, which also limits the usable thickness of the substrate material.

Figure 4:
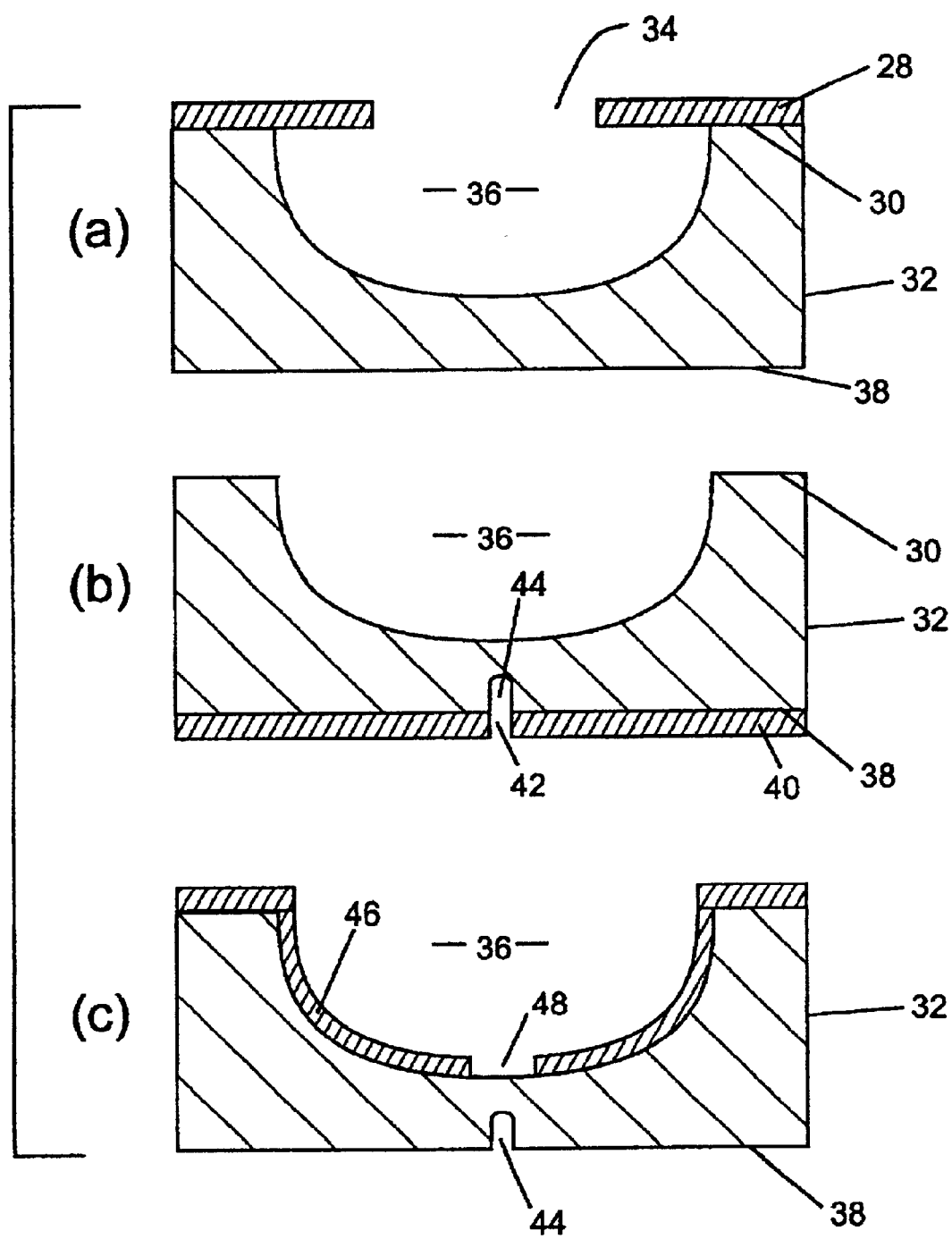
FIG. 4 is a schematic illustrations of the initial and intermediate etching steps followed to manufacture patch-clamp electrode apertures suitable to practice the invention.

Accordingly, a convenient method for fabricating holes in the substrate involves the steps illustrated in FIG. 4. The substrate 32 may be a plate of glass or other suitable material with a thickness of about 100 microns (the thickness of a typical microscope cover glass). As illustrated in part (a) of the figure, the first step in the process involves the formation of a photoresist mask 10 on the surface 30 of one side of the substrate 32 with an array of small openings 34 (only one opening is illustrated in the figures for simplicity) considerably larger in diameter (about 100 $\mu$m) than the desired diameter of the final electrode apertures (about 0.5–10 $\mu$m). A small notch 36 (not a through-hole) is then etched into the substrate 32 by isotropic etching through each small opening 34 in the photoresist mask 28. During this first etching step, the opposite side 38 of the glass substrate 32 is protected from etching by a suitable protective layer (not shown). The depth of the notch 36 is judiciously made slightly smaller than the thickness of the substrate 32, so as to avoid its perforation. For example, if the substrate 32 is 100-$\mu$m thick, the notch 36 could be etched to a depth of about 80 $\mu$m, leaving a thickness of about 20 $\mu$m from the bottom of the notch 36 to the opposite side 38 of the substrate 32.

During the second step of the process, illustrated in part (b) of FIG. 4, the layer of photoresist 28 and the protective layer on the bottom surface 38 of the substrate 32 are removed using standard photoresist stripping techniques from semiconductor processing. Another layer of photoresist 40 is then deposited on the bottom side 38 of the substrate 32 and an array of small holes 42, each positioned below a corresponding well 36, is opened in the photoresist layer 40. The diameter of the holes 42 is made equal to or smaller than the desired diameter of the final electrode apertures to be produced. The top side 30 of the glass substrate 32 (including the wells 36) is covered with a protective layer (not shown in the figures). A small (not through) opening 44 is then etched into the glass through each hole 42 in the photoresist mask 40, either by isotropic or anisotropic methods.

In a third step of the etching procedure illustrated in part (c) of FIG. 4, the photoresist layer 40 and the protective layer on the top side 30 of the substrate 32 are stripped away. Another layer of photoresist 46 is deposited on the top surface 30 of the substrate 32 also to cover the bottom of the wells 36 created by the first step. An opening 48, smaller than the opening 34 used-in the first step (e.g., about 20 microns in diameter), is created in the photoresist layer 46 at the bottom of each well 36 and opposite to the small hole 44 etched from the bottom of the substrate 32 during the second step of the procedure. Finally, the bottom surface 38 of the substrate 32 is brought into contact with a conductive water-based solution (such as a solution of NaCl), and the solution is sonicated to wet all the small holes 44 created in the second step.

Figure 5:
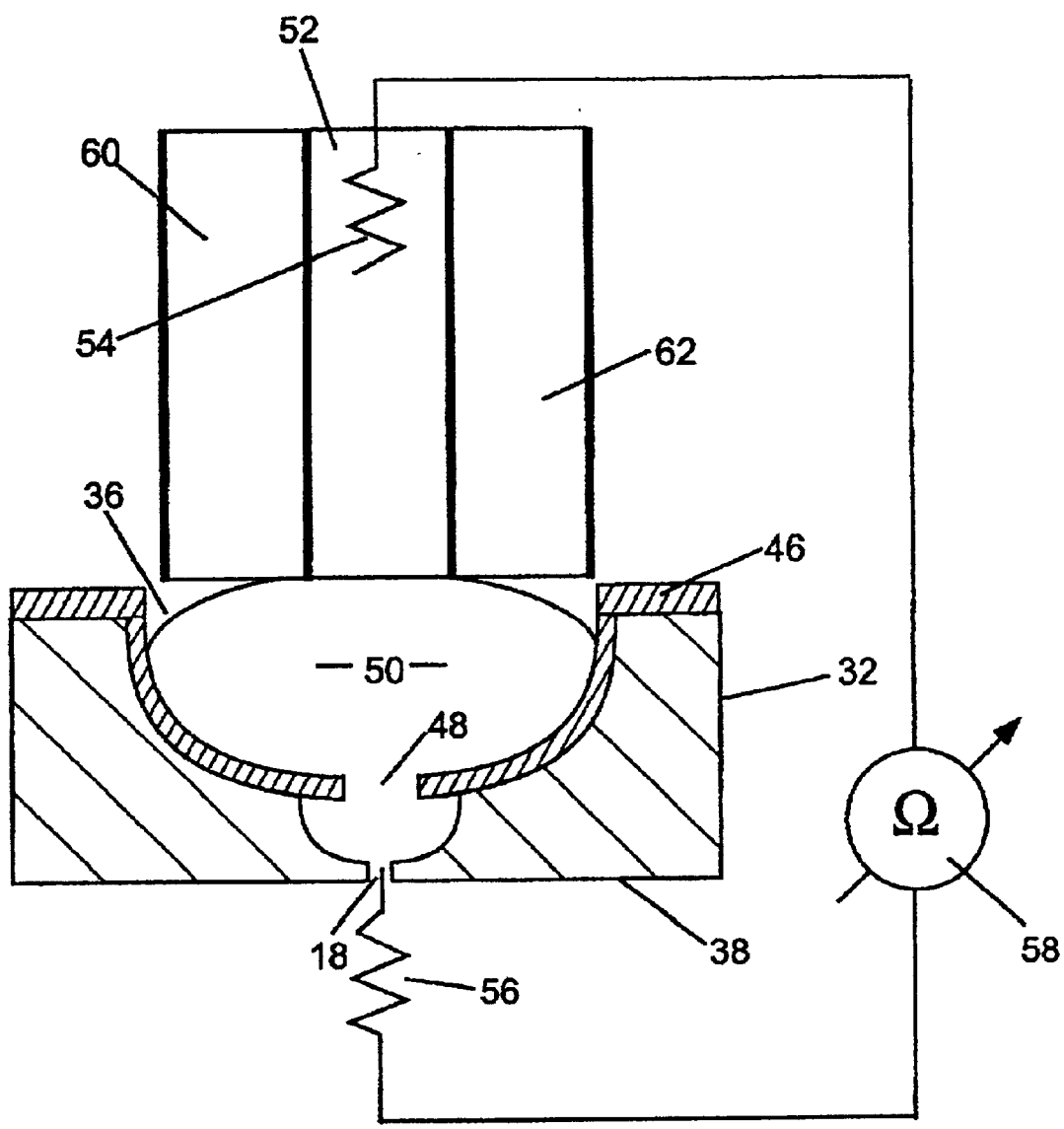
FIG. 5 is a schematic illustration of the final etching step followed to manufacture a partition plate according to the procedure of FIG. 4.

Finally, a small drop of etchant solution 50 (such as a dilute solution of hydrofluoric acid) is deposited into each well 36 in the substrate 32 from a small pipette 52, and brought into contact with the opening 48 in the photoresist layer 46, as illustrated in FIG. 5. An electrode 54 (such as an Ag/AgCl electrode) is brought into contact with the drop of etchant solution 50 in the well 36, while another electrode 56 is immersed in the saline solution contacting the bottom side 38 of the substrate 32. The resistance between the two electrodes 54,56 is monitored by an ohmmeter 58. As soon as the substrate 32 is etched through, the etching solution 50 is permeated with the saline solution filling the small holes 44 at the bottom of the substrate 32, which causes the resistance between the two electrodes to decrease sharply. A control microcomputer (not shown) is preferably used to detect the decrease in resistance and subsequently activate a wash cycle during which water is squirted into the newly etched opening 18 from a separate rinse tube 60, and excess water is sucked away by a third tube 62. As a result of this multistep operation, each small hole 44 is converted into an electrode aperture 18 for patch-clamp measurements. After completion of the etching cycle, the photoresist layer 46 is removed from the substrate 32.

In the manufacture of electrode plates with large arrays of individual electrode apertures for massive parallel testing, as envisioned by the invention, the typical distance between electrode apertures 18 in the substrate plate 32 is about 2 mm. This process can be carried out separately for each single electrode aperture 18 (one at a time) or in parallel for the entire array of electrode apertures. In the former case, the set of tubes 52,60,62 and the electrodes 54,56 are moved and aligned with each new opening 34 in the photoresist 28 after each electrode aperture 18 is formed, and the cycle of etching/washing is repeated until all holes in the substrate 32 are opened. The final layer of photoresist 46 is then stripped off the substrate. In the case where all electrode apertures are etched simultaneously, the same etching solution is used to contact at the same time all appropriate portions of the surface of the substrate's blank. We found that, since the same etching conditions apply for all holes (concentration of etchant, temperature, plate thickness, etc.), the rates of etching of neighboring wells are virtually the same (within less than 1% variation). Therefore, all the wells on the substrate may be etched together while monitoring progress by measuring the resistance across the plate. This allows for a great increase in productivity in the fabrication of patch-electrode plates.

Figure 6:
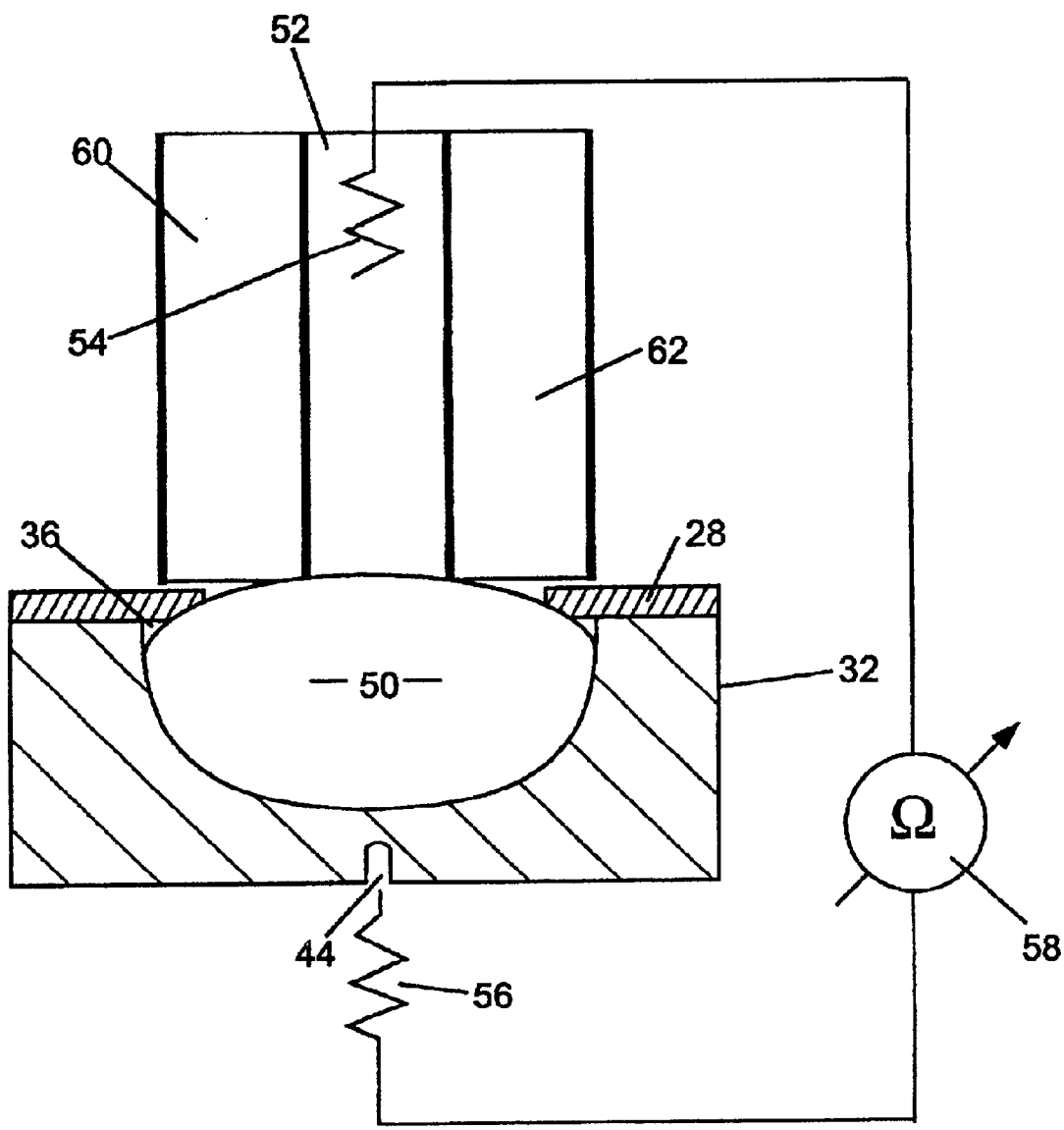
FIG. 6 is a schematic illustration of the final etching step of an alternative procedure for manufacturing a partition plate for the invention.

According to a simpler, alternative process, the third step of FIG. 4 is bypassed and the substrate of part (b) in that figure is etched directly through the original photoresist mask 28, as illustrated in FIG. 6. While this shortcut reduces the number of manufacturing steps, the time necessary to wet etch the well 36 in the substrate plate 32 is increased because a slow etching solution 50 has to be used in order to control the process and stop etching progress upon completion. Therefore, this procedure is not preferred.

Figure 7:
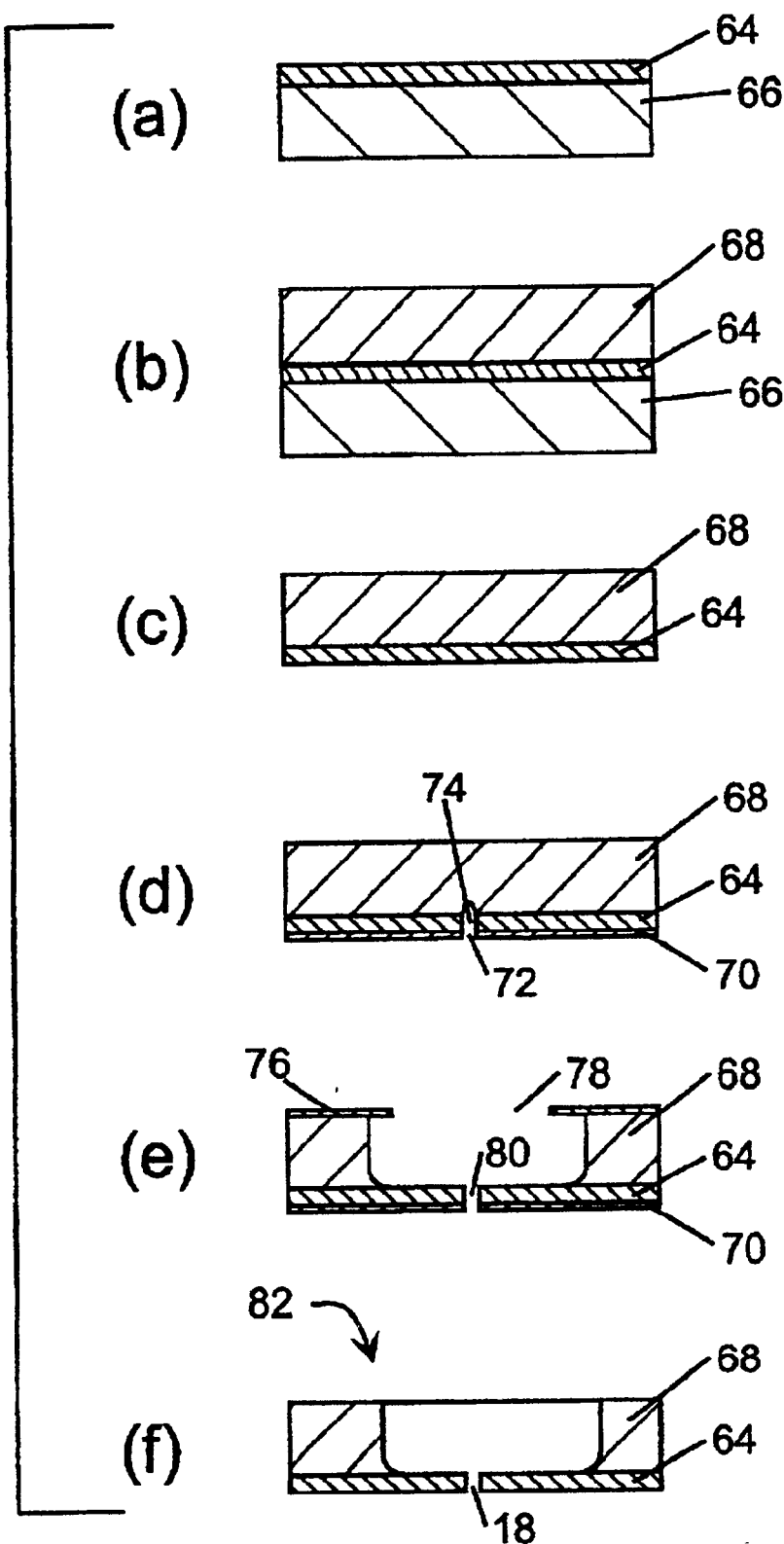
FIG. 7 contains schematic illustrations of the various etching steps followed to manufacture a partition plate from a silicon substrate.

When silicon material is used to manufacture the electrode plate of the invention, a different etching procedure may be followed, as illustrated in FIG. 7. In the first step, shown in the figure as part (a), a thin layer 64 (in the order of several microns) of silicon dioxide is developed on one surface of a silicon substrate 66 by any known process, such as, for example, thermal oxidation. Then, as shown in part (b) of the figure, a layer 68 of boron silicate glass (BSG) is deposited on top of the silicon dioxide layer 64. The BSG has a low melting temperature (<500° C.), so that it can be melted and reflown to create a planar layer, as illustrated, according to a practice that is well known in the art of semiconductor processing.

As shown in part (c) of FIG. 7, the remaining layer of silicon substrate 66 is then etched away, using etchant material that selectively etches silicon but not glass or silicon dioxide. A photoresist mask 70 is deposited on the silicon dioxide layer 64 with small openings 72 corresponding to the intended locations of the electrode apertures to be built into the substrate, and the silicon dioxide layer is etched (anisotropically) to create a hole 74 about 1 $\mu$m in diameter through the silicon dioxide layer 64, as illustrated by part (d) of FIG. 7. Another photoresist mask 76, with a larger opening 78, is then deposited on top of the BSG layer 68, and the boron silicate glass is etched away with an etchant solution that selectively etches BSG but not silicon dioxide, thereby forming a through aperture 80, as shown in part (e) of the figure. Finally, the photoresist masks 70,76 are stripped away, leaving a partition plate 82 with electrode apertures 18 suitable for forming a high-resistance seal with a biological membrane for patch-clamp electrophysiological recording.

Thus, several methods have been described to produce plates with arrays of electrode apertures to practice parallel testing of a plurality of test cells. In order to accomplish the goals of the invention, each electrode aperture must be incorporated into a perfusion chamber containing an extracellular compartment, where the test cells are suspended in an extracellular solution to form a seal with the electrode aperture, and an intracellular compartment electrically connected to an electrode through an intracellular solution. Each chamber must also be connected to a fluidic system with appropriate valving and pressure/vacuum sources to feed and withdraw the extracellular and intracellular solutions through the appropriate compartments and channels in the chamber, as done for conventional electrophysiological recording. Because of the miniaturization required by the use of large arrays of chambers, so that massive parallel testing can be carried out, the alignment of the various components making up such a structure is critical and difficult to achieve with conventional fabrication practices. Therefore, according to another aspect of the invention, the etching methods described above may be advantageously utilized to also form all fluid-flow channels, tubes and cavities required to integrate the patch-hole plate into a working electrode assembly.

Figure 8:
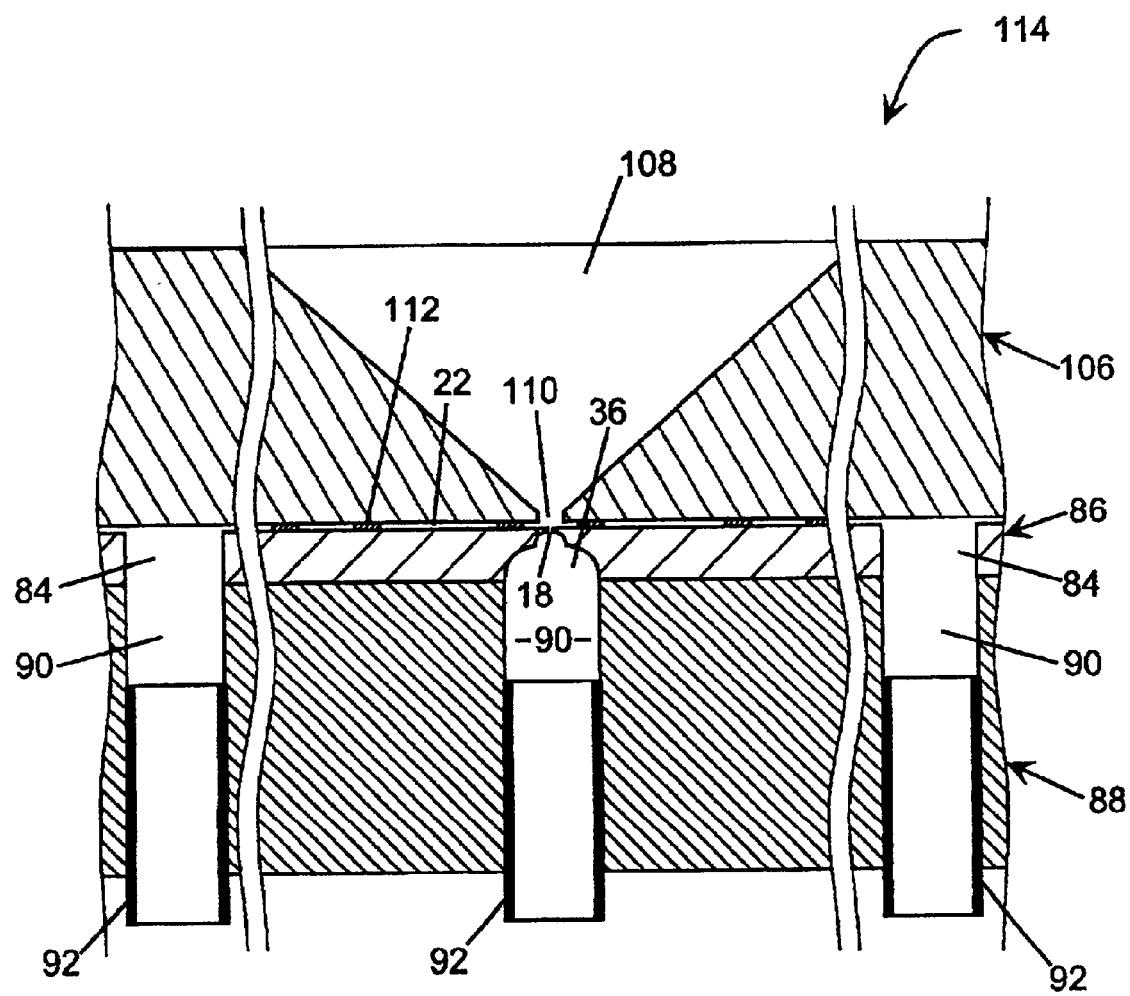
FIG. 8 is a schematic sectional view of a removable unit constituting the upper portion of a multi-chamber electrode assembly according to the invention.

Accordingly, in addition to the series of wells and openings leading to the formation of the electrode apertures 18, the same techniques may be used to etch larger through channels 84 through the substrate of interest, as seen in FIG. 8. Given the array configuration of the electrode apertures 18, the channels 84 are preferably spaced between them so that there is essentially one fluid-flow channel for each electrode aperture in the substrate. These fluid-flow channels, which are used to transport extracellular solution, may be etched before or after etching of the electrode apertures.

Thus, in the process of manufacturing of a multi-chamber electrode assembly for parallel testing according to the invention, a partition plate 86 (or a comparable plate produced by another process, such as the one illustrated in FIG. 7), with the appropriate number of electrode apertures 18 to form the desired array of perfusion chambers, is cemented to another, thicker, "foundation" plate 88 made of glass or plastic or other suitable insulating material. Any suitable adhesive, such as epoxy adhesive, can be used to cement the plates. The thicker foundation plate 88 has a number of channels 90, made by etching or drilling a blank or by molding or embossing during the plate manufacture, which are aligned with corresponding channels 84 and wells 36 in the partition plate 86. The preferred thicknesses of the partition plate 86 and foundation plate 88 are about 0.1 mm and 1 mm, respectively, and the diameter of the channels 84,90 and wells 36 is about 0.2 mm. Each channel 90 in the foundation plate 88 must be perfectly aligned with a corresponding channel 84 or well 36 in the partition plate 86 when the plates are cemented, as shown in FIG. 8. In addition, each channel go has a metal electrode tube 92 or an equivalent structure inserted (press fitted) into it to provide a conductive surface in the channel. The electrode tube 92 is made of a metal that provides good electric contact with an intracellular solution; for example, a silver tube covered with a film of silver chloride (Ag/AgCl) has been found to be an effective material.

Figure 9:
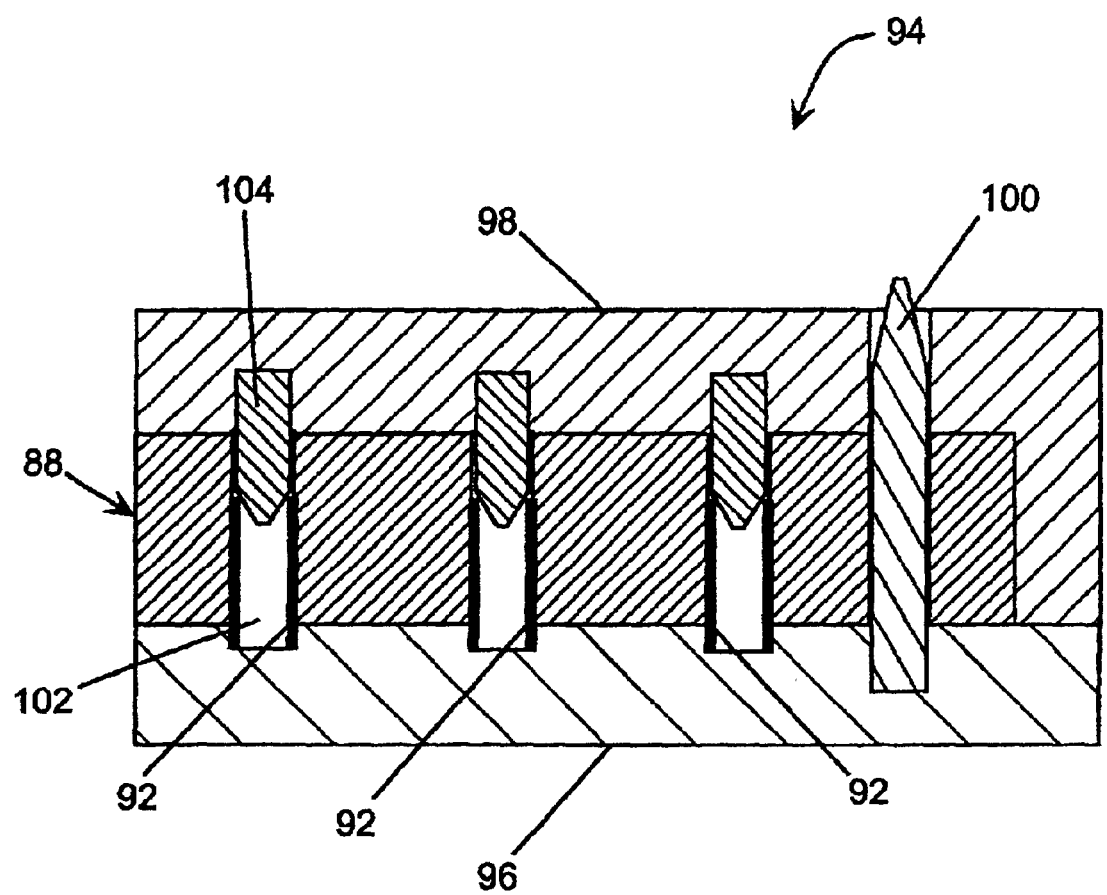
FIG. 9 is a schematic view of a molding form for fabricating the foundation plate used in the removable unit of FIG. 8.

The preferred way of manufacturing the foundation plate 88 is by molding from a moldable plastic. As illustrated in FIG. 9, a molding form 94, preferably made of steel, contains two opposite parts 96,98 separated by a distance that determines the thickness of the plate 88. The two parts 96,98 are aligned using a locating pin 100. The bottom part 96 of the form 94 has a number of small openings 102 equal in diameter to the outer diameter of the metal electrode tubes 92 to be inserted into the foundation plate 88. The top part 98 of the form contains a number of pins 104 used to hold the tubes 92 in place during the molding process. Thus, the tubes 92 are inserted into the openings 102 in the bottom part 96 of the molding form and the two parts are assembled together. Then, the form 94 is filled with moldable plastic using standard plastic molding techniques. Finally, the two parts 96,98 of the form 94 are disassembled and the foundation plate 88 is released with the channels 90 and corresponding electrode tubes 92 molded in place.

Alternatively, the foundation plate 88 may be manufactured with channels 90 from any suitable plastic material by drilling holes with a conventional drill through a blank, or by etching holes through a glass blank while protecting exposed surfaces with a suitable protective film. For example, the photoresist material used as a mask to etch the holes in the partition plate described above could serve as such a protective layer, or the layer could consist of an adhesive film placed on the surface of the plate before drilling the hole. As an alternative to the electrode tubes 92, the internal surface of the channels 90 and the surface of the protective film could then be metallized to form an electrode surface equivalent to the tubes 92. This could be accomplished, for example, by depositing a metal film in a sputtering process. The protective film would then be removed, either by peeling it (if adhesive) or by stripping it (if photoresistive), leaving the internal surface of the channels 90 in a metallized condition. Other processes for metallizing the channels 90 in the foundation plate 88 could be used with equivalent results, such as by electroplating, as done in the manufacture of printed circuit boards.

Referring back to FIG. 8, an additional component, a "chamber" plate 106, is attached to the opposite side of the partition plate 86. The chamber plate 106 is preferably made of plastic by molding or embossing (with a preferred thickness of about 1 mm) and contains an array of funnels 108 corresponding to the electrode apertures 18 in the partition plate 86. Each funnel 108 is preferably conical with a lower opening 110 through the chamber plate 106 vertically aligned with the small electrode aperture 18 in the partition plate 86. The opening 110 in the small part of the funnel 108 functions as a "cell locator" hole, preferably with a diameter close to but slightly larger than the diameter of the test cell 14 being studied. According to an important aspect of the present invention, the chamber plate 106 is separated from the partition plate 86 by a plurality of appropriately distributed spacers 112, such as small protrusions molded or hot-embossed into the structure of the chamber plate during the fabrication. The spacers 112 maintain a gap corresponding to the channel 22 in FIG. 1, preferably about 5 $\mu$m in height, between the chamber and the partition plates. Thus, the chamber, partition, and foundation plates 106,86,88 (FIG. 8) together constitute a removable single unit 114 for the upper portion of a multi-chamber electrode assembly according to the invention. Because of its relative ease of fabrication with the processes disclosed herein, it is expected that the unit 114 will be treated as a disposable component of the apparatus.

In an alternatively process of manufacture, the foundation plate 88 of the electrode array can be made (preferably molded) from silicon rubber or other suitable insulating elastic material. As illustrated in the unit 116 of FIG. 10, the plate 88 can be shaped to include integral O-rings 118 around the through-holes 90, so as to provide a tight seal when the unit 116 is mounted onto a receiving component in the electrophysiological recording equipment. As in the case of unit 114, the channels 90 in the foundation plate 88 of the unit 116 may have electrode tubes 92 inserted into them, or may alternatively be covered with a conductive film (such as AgCl).

Figure 11:
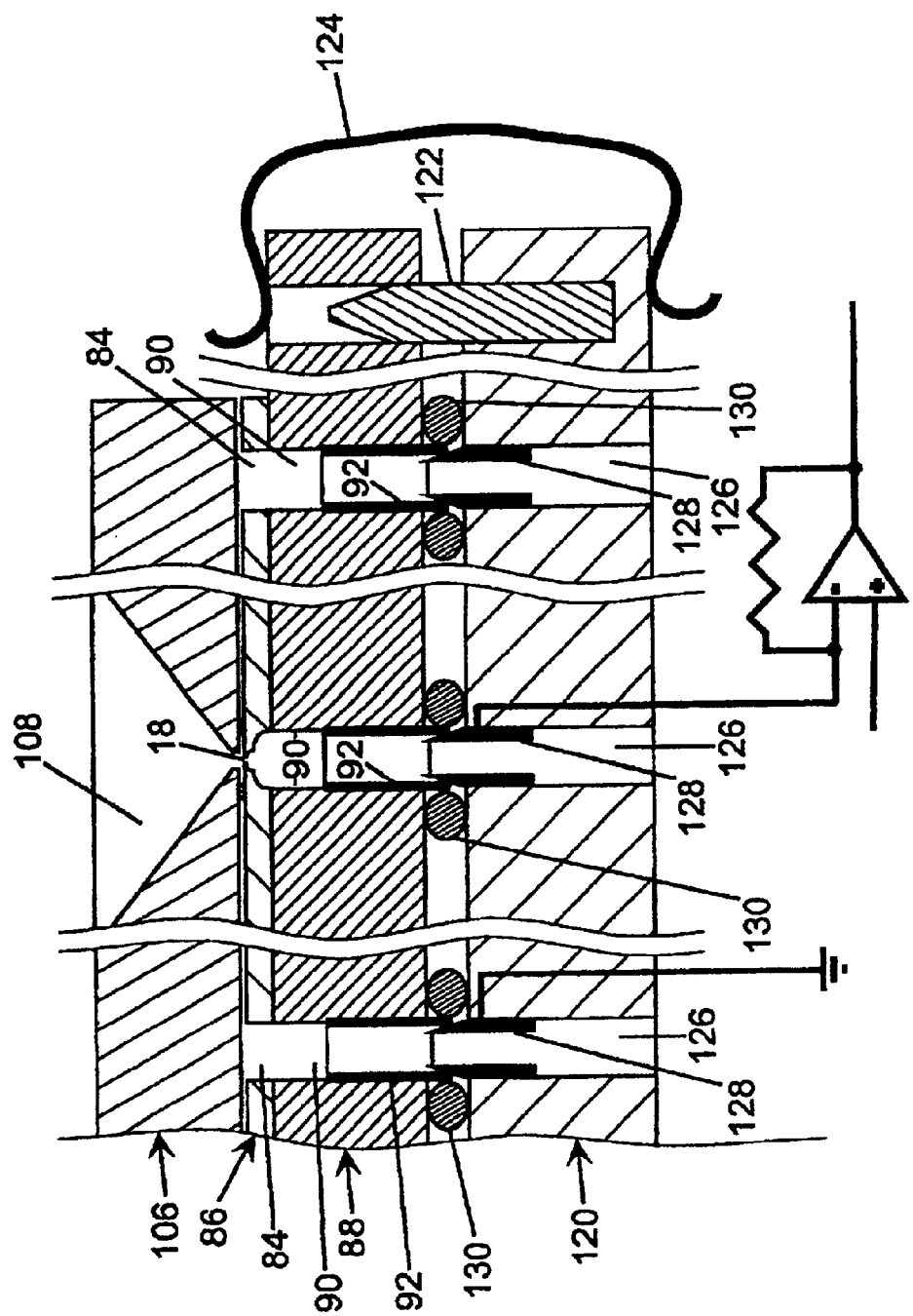
FIG. 11 is a schematic sectional view of a multi-chamber electrode assembly according to the invention consisting of the disposable unit of FIG. 8 mounted on a permanent structure using alignment pins and clamps.

As illustrated in FIG. 11, the disposable unit 114 (or 116) of the invention is coupled to a non-disposable structure 120 using alignment pins 122 and clamps 124. Each channel 90 in the disposable unit 114 has a corresponding counterpart channel 126 in the permanent structure 120. The channels 90,126 are connected via mating couplers 128, which consist of short metal tubes with a frustoconical tip for alignment with and tight engagement of the electrode tubes 92. The couplers 128 that, through their connection to the tubes 92, are aligned with the electrode apertures 18 in the partition plate 88, in addition to providing hermetically sealed coupling, also serve as electric contacts to the Ag/AgCl (or some other suitable material) electrode tubes 92 in the disposable unit 114. Each coupler 128 corresponding to an electrode aperture 18 in the partition plate 86 is thus electrically connected in conventional fashion to an individual current-voltage converter unit. Each other coupler 128 connected to Ag/AgCl tubes 92 associated with larger fluid-flow channels 84 in the partition plate 86 is instead connected to electrical ground. Optional rubber O-rings 130 are preferably placed around the couplers 128 to make sure the contacts between the channels are hermetically sealed.

Figure 12:
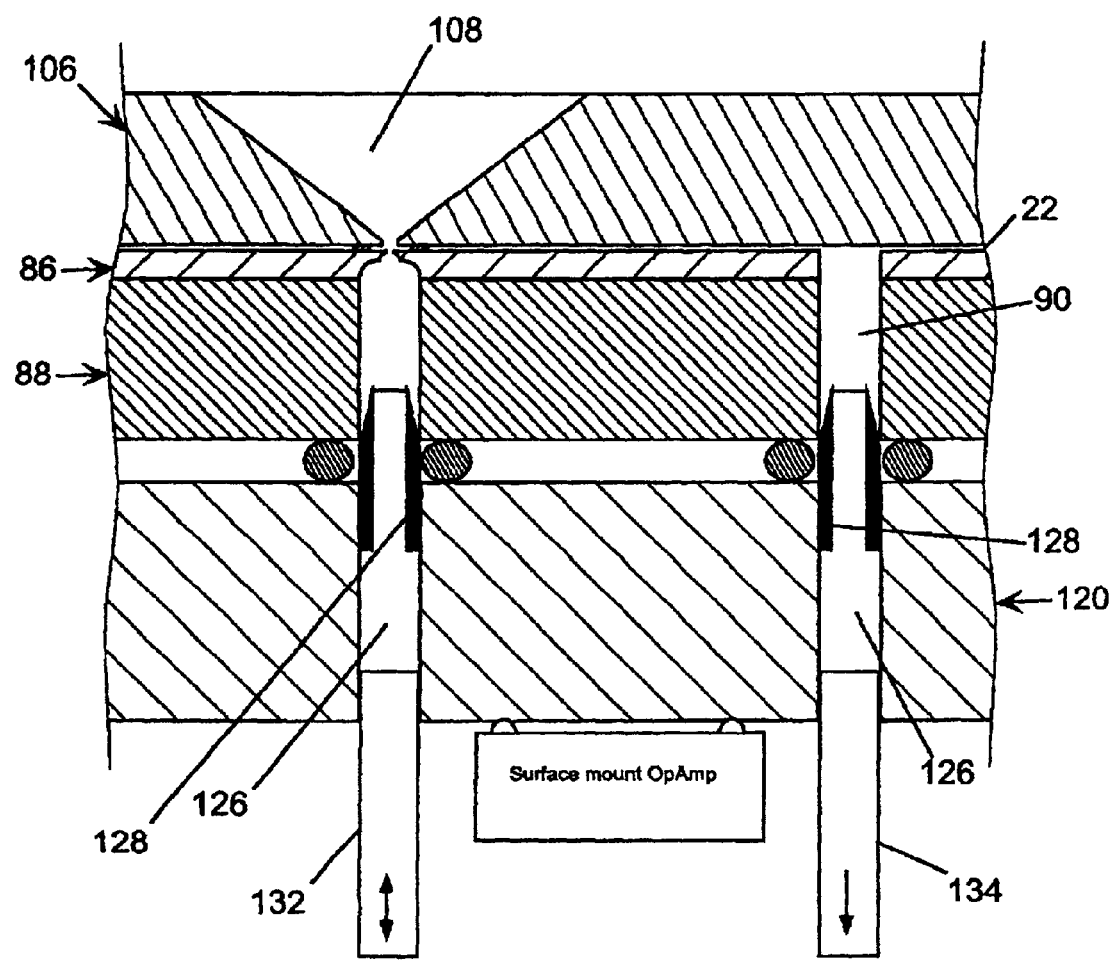
FIG. 12 is a schematic sectional view of an alternative embodiment of the multi-chamber electrode assembly of FIG. 11.

Another way of making the patch-clamp apparatus of the invention could be to have elongated metal couplers 128 molded or otherwise fabricated in the permanent structure 120 so as to extend into the channels 90 of the disposable unit 114, as illustrated in FIG. 12. This would eliminate the need for the electrode tubes 92, considerably simplifying the fabrication of the disposable unit. Since the couplers 128 consists of Ag/AgCl tubes that usually do not last too long, a disadvantage of this simplification is the fact that the non-disposable part of the apparatus may have a shorter life, thereby rendering it essentially semi-disposable.

The channels 126 in the permanent structure 120 are connected to sources of regulated pressure and vacuum via computer controlled valves (not shown) and tubing 132,134, as illustrated schematically in FIG. 12. Conventional electromagnetic valves can be used, but micromachined valves are preferred. Such micromachined computer controlled valves are known in art. The tubing 132 inserted into the structure 120 connects the electrode-aperture channels to suction and the tubing 134 connects the extracellular fluid-flow channels to pressure/suction via the control valve system.

Figure 13:
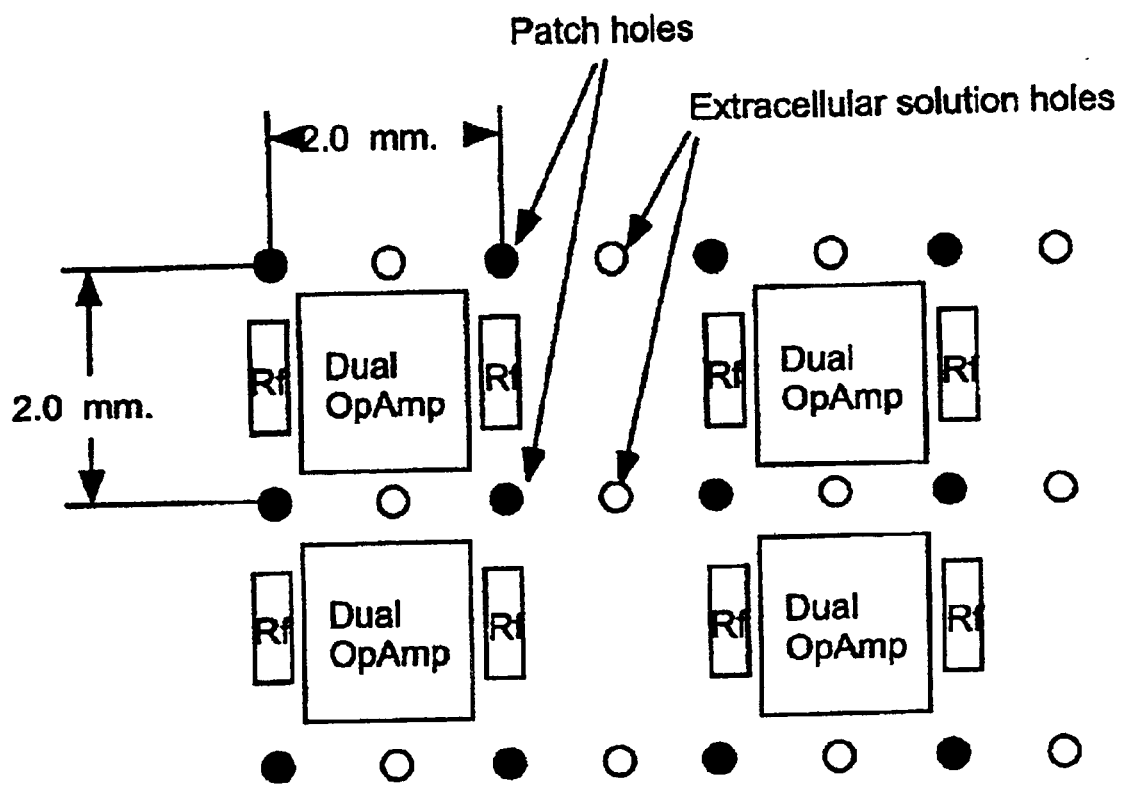
FIG. 13 is a diagram of the layout of the patch-hole and fluid-flow hole matrix in the electrode assembly of the invention.

The permanent structure 120 is preferably made of a Teflon® printed circuit board, with all connections between electrodes and amplifiers printed on the board. Microminiature operational amplifiers, such as OpAmps in microSMD packaging, are preferably used. The dual OpAmp in a microSMD package has outside dimensions of 1.28×1.28× 0.7 mm, with ball grid array leads. Together with the surface mount feedback resistors (Rf), the two channels of the current amplifier fit into a footprint about 1.3×3 mm. Therefore, free space is left for electrical traces and for fluidic channels 128 for connection with electrode apertures 18 and fluid-flow channels 90. A 2-mm spacing between channels may be achieved, as illustrated in FIG. 13.

Figure 10:
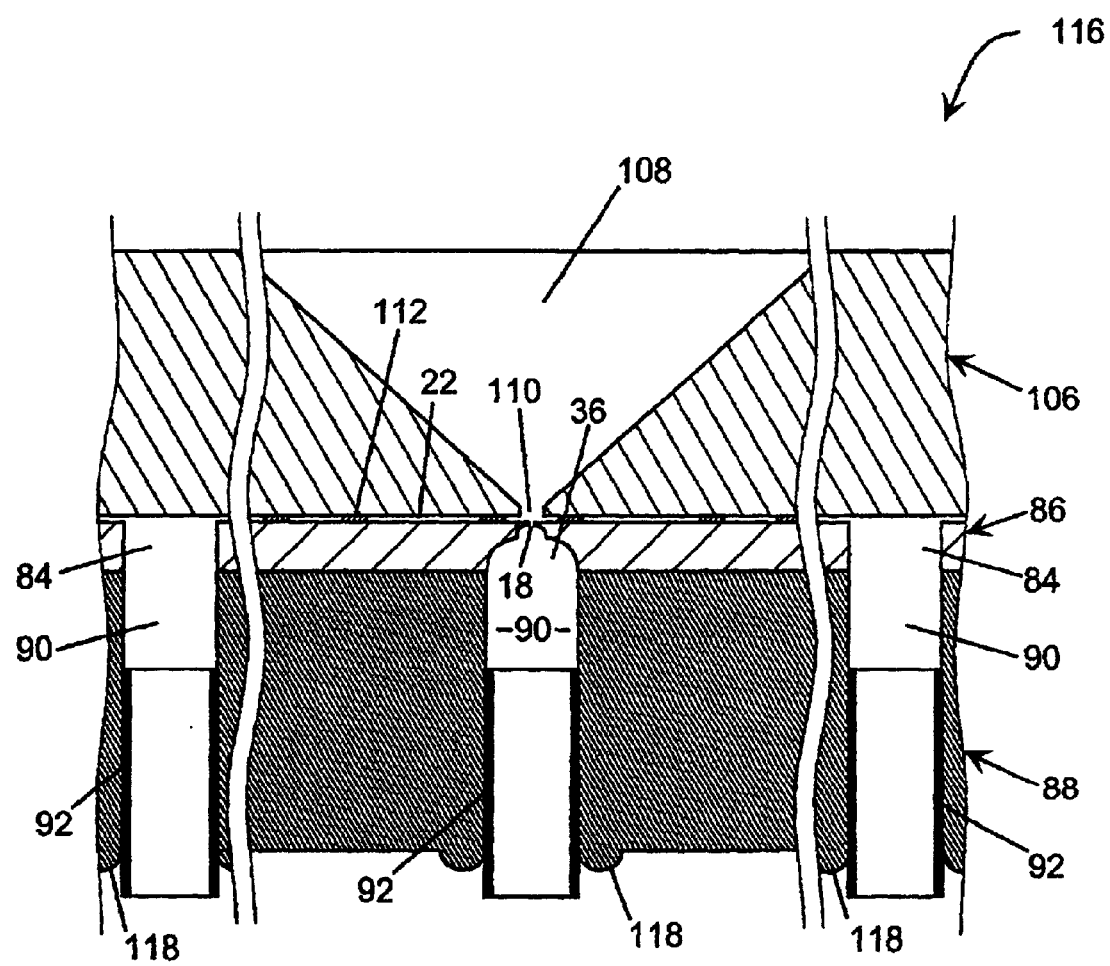
FIG. 10 is a schematic sectional view of an alternative embodiment of the removable unit constituting the upper portion of the multi-chamber electrode assembly of the invention.
Figure 14:
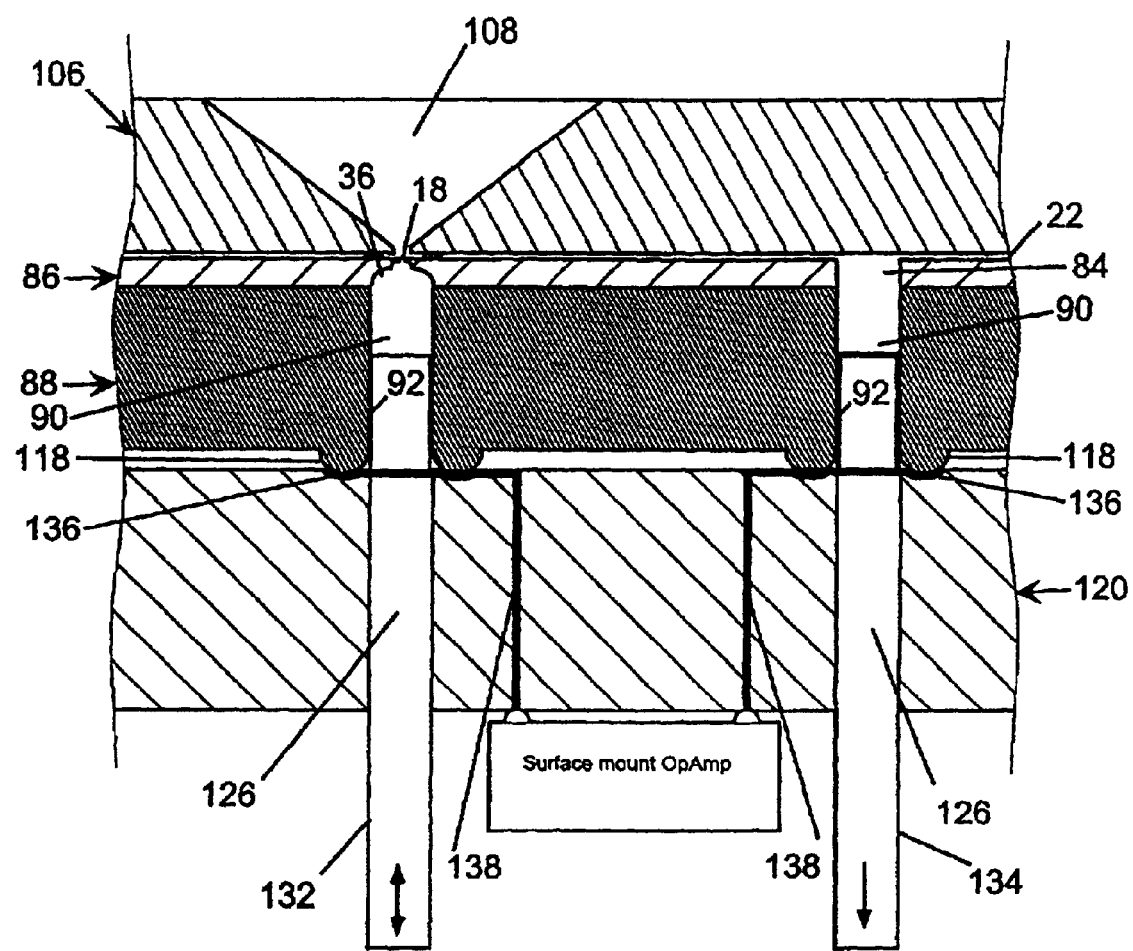
FIG. 14 is a schematic sectional view of another embodiment of the multi-chamber electrode assembly of FIG. 11.
Figure 15:
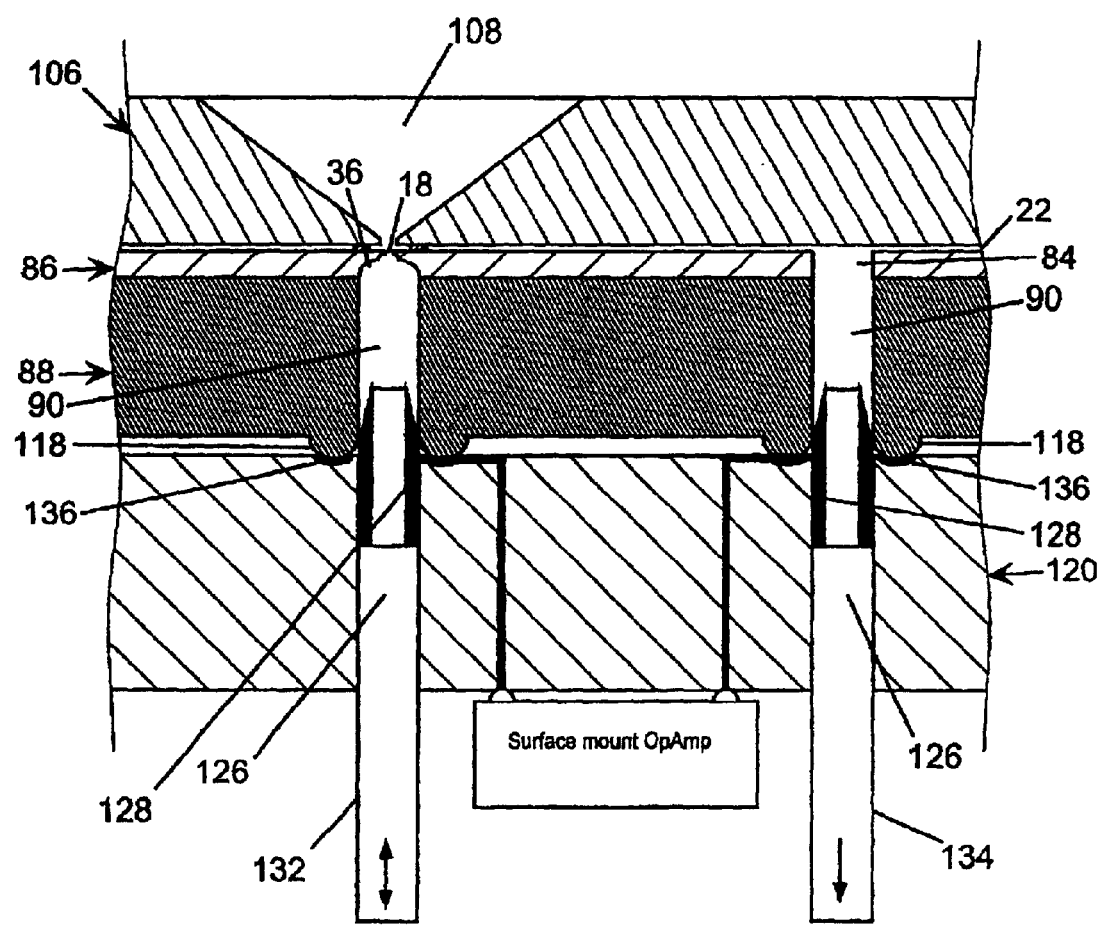
FIG. 15 is a schematic sectional view of yet another embodiment of the multi-chamber electrode assembly of FIG. 11.

An alternative way of making the apparatus of the invention is shown in FIG. 14, where the disposable unit 116 of FIG. 10 is used. The foundation plate 88 made of silicon rubber with integrated O-rings 118 is fitted into corresponding small groves 136 in the permanent structure 120, which serve to align the integrated O-rings and maintain a hermetic seal between the channels 126 and 90. The bottoms of the grooves 136 are metallized (using standard printed-circuit-board making techniques) to provide electrical connection with Ag/AgCl tubes 92 molded into the silicon rubber plate 88. The metallized grooves 136 are connected to the electronics of the system by printed traces 138. If no Ag/AgCl electrodes 92 are integrated into the foundation plate 88, couplers 128 may instead be used inserted (press fitted or otherwise) into the non-disposable structure 120 as illustrated in FIG. 15.

Figure 16:
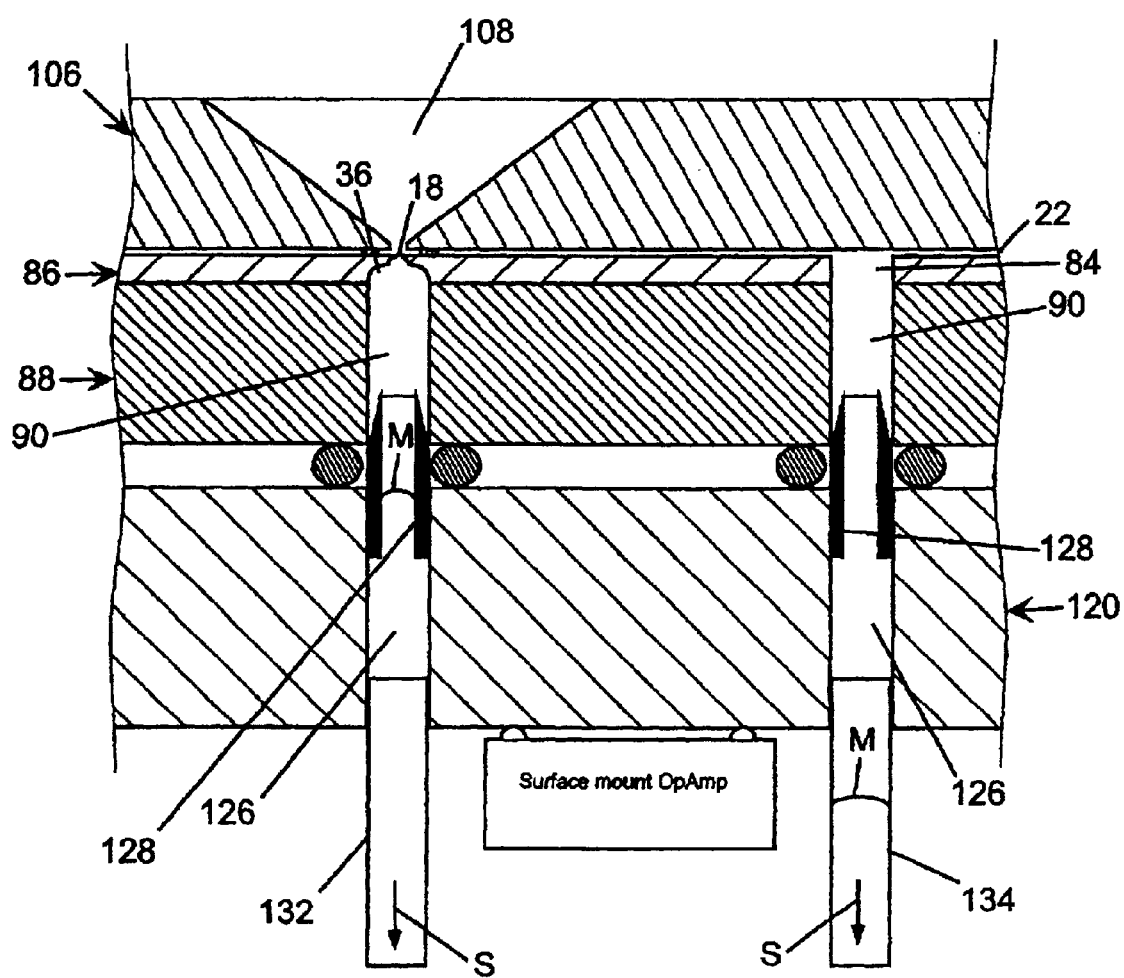
FIGS. 16 and 17 are schematic views illustrating the process of priming the electrode assembly of the invention.

Before use, the apparatus of the invention needs to be primed with appropriate extracellular and intracellular solutions. For this purpose, the disposable unit 114 (or 116) is coupled to the non-disposable structure 120, which is connected to electronics, valves, and pressure/suction sources, and the resulting electrode assembly is placed in the bottom of a reservoir. All solutions to be used for priming and testing are pre-filtered to eliminate contaminants that could block fluid-flow holes. The reservoir is filled with the solution to be used as the intracellular fluid, so as to completely immerse the electrode assembly. As illustrated by arrows S in FIG. 16, suction is applied to both tubes 132,134 connected to the channels leading to the electrode apertures 18 and the larger fluid-flow channels 84, thereby causing the solution to be drawn through the holes to fill all channels 90 and 126 in the disposable and permanent parts of the apparatus. Since the channels 84 in the partition plate 86 have much larger diameter than the electrode apertures 18, they are filled much more quickly (through the channels 22 in the gap between the partition and chamber plates) than the wells 36 below the electrode apertures, so that after some time suction through the channels 84 (also referred to as extracellular channels) is turned off by closing the associated valves. Since the electrode apertures 18 are much smaller, the suction is maintained through the electrode apertures until there is enough solution drawn through the holes to wet the electrode associated with each electrode aperture (also referred to as the intracellular channel; the metallic coupler 128 in the embodiment of FIG. 16). This event is sensed by the control computer when a sharp drop in the resistance between the extracellular and intracellular channels is detected. After waiting for some more time to fill a good portion of the channels associated with electrode apertures, suction through the electrode apertures (tubes 132) is turned off by closing the associated valve. As the internal diameter of these channels is small (about 0.2 mm), the intracellular solution sucked into them will form a meniscus M that will prevent it from draining out of the series of conduits 90,128,126. Flow through the electrode apertures may be facilitated by also applying positive pressure to the reservoir, so that the resulting pressure differential driving the solution through the electrode apertures may be significantly greater than what can be achieved by suction alone.

Figure 17:
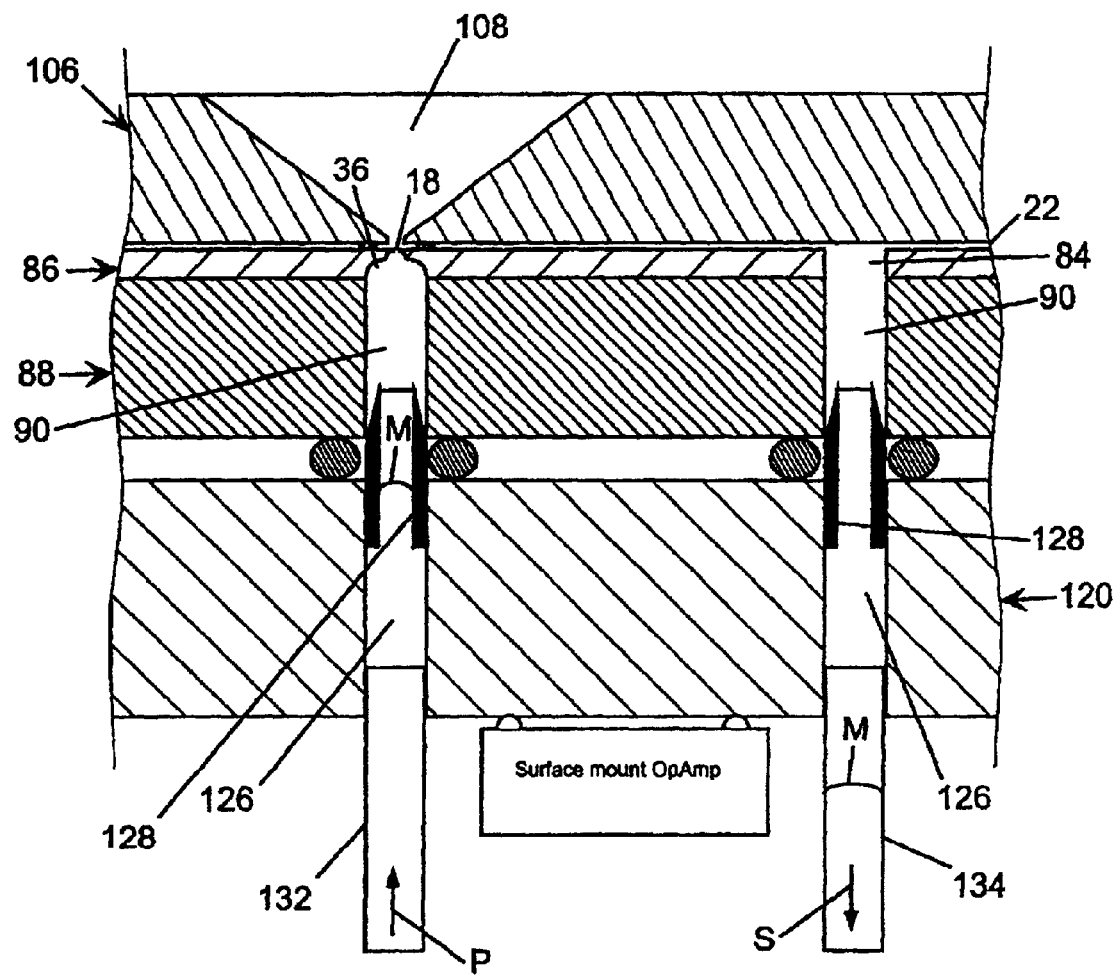

After priming the electrode apertures 18 with intracellular solution, the fluid in the reservoir is replaced with extracellular solution. A small positive pressure is applied to the channels leading to the electrode apertures (by opening appropriate valves), as illustrated by arrow P in FIG. 17, so that intracellular solution is slowly passed upward through each electrode aperture 18 without possibility of extracellular solution flowing downward through the electrode aperture. The suction through the extracellular channels (tubes 134) is turned on again, as illustrated by arrow S in the figure, so as to draw enough extracellular solution inside the funnels 108, channels 22, and extracellular conduits 84,90, 128,126 to replace the intracellular solution previously present in those voids.

In operation, after priming with the appropriate solutions as indicated, a suspension of free-floating cells, preferably uniformly sized, is placed into the extracellular solution in the reservoir. The solution in the reservoir is agitated slightly, to assure random even distribution of the cells. As the cells settle down, small suction is applied through the extracellular tubes 134 to draw the solution through the funnels. At the same time, a small positive pressure is maintained to the electrode apertures through tubes 132 to assure that no extracellular solution flows downward through the electrode apertures, according to the invention. Additional pressure may be applied to cause perfusion of intracellular fluid into the extracellular compartment if deemed desirable. The test cells are thus being drawn by the flow of extracellular solution and by gravity until one of them reaches the opening 110 at the bottom of a particular funnel 108. This event is sensed by the control computer by measuring the resistance through the associated electrode aperture 18 via a corresponding current-voltage converter, as already practiced in the art. (The same sensing system may be used to detect the direction of fluid flow through the electrode aperture based on the difference in electrical conductivity between the extracellular and intracellular solutions.) The cell, settling down on the bottom of the funnel, obscures the electrode aperture and increases the resistance. This phenomenon typically occurs when the cell is within a radius of about twice the diameter of the electrode aperture from the edge thereof. When the computer senses this change, it activates suction through the corresponding electrode aperture 18 (tube 132) by opening and closing the appropriate valves. The suction pulls the cellular membrane toward the electrode aperture, establishing a seal between the hole in the partition plate and the cellular membrane. The progress of sealing can also be monitored by the computer by measuring the leakage resistance through the electrode aperture.

After establishing the seal (a high-resistance seal, typically a giga-seal), the computer opens another valve connected to the patch circuit (tubes 132) to apply a momentary much higher pressure to the electrode aperture. This ruptures the part of the membrane sucked into the electrode aperture, establishing access to the cell's interior through the electrode aperture (whole-cell patch-clamp configuration). Rupturing the membrane can be facilitated by also applying a large voltage across the membrane via a voltage control from the computer to the current-voltage converter. After a high-resistance seal is established, the remaining cells in the perfusion chambers are preferably washed away by perfusing the chamber with excess extracellular solution. After this procedure is completed, the current through the test cell's membrane can be measured while the voltage across the membrane is controlled, according to conventional patch-clamp recording.

It is noted that this procedure of sealing the cells to the electrode apertures can be carried out independently and simultaneously in all chambers of the apparatus (several hundred chambers are currently being considered). If some of the chambers do not contain cells (as might occur as a result of low cell density), more cells may be added until enough cells are sealed (less than 100% may be acceptable). After the test cells are sealed, extracellular solution with various drugs is added into the reservoir under computer control using standard solution handling devices (such as automatic pipettors), and the cellular response is studied. It is also possible to study currents through the patch of the membrane sealed into the electrode aperture without rupturing the membrane (that is, in extracellular patch-clamp configuration).

The electrode assembly of the invention is particularly suitable for constructing an apparatus to conduct massively parallel, high-throughput patch-clamp recording for drug screening. The apparatus may consist of a multiplicity of the multi-chamber cell-recording assemblies described above (FIG. 15, for example). Each assembly may have many (up to several hundred) perfusion chambers and corresponding recording channels. Each assembly may be placed in a separate solution reservoir, so that it is an integral part of the bottom of the reservoir. Each reservoir may be accessible, through an intake port and an outlet port, to automatic solution handling devices, such as air-pressure pipettors or positive-pressure displacement pipettors, that are well known in the art. These may be used to deliver the various solutions to the reservoirs. The solution-handling devices may also be used to deliver the test cells to the reservoirs.

Thus, one aspect of the invention demonstrates that the detrimental mixing of extracellular fluid with intracellular fluid in the intracellular compartment of a perfusion chamber is avoided by appropriately controlling the pressure across the electrode aperture. According to another aspect of the invention, the test cells in the extracellular compartment are directed toward the electrode aperture by the extracellular fluid flow while at the same time preventing its flow through the aperture; when a cell approaches the aperture, it is then drawn in to it to form a patch-clamp seal by applying suction from the intracellular compartment.

Figure 18:
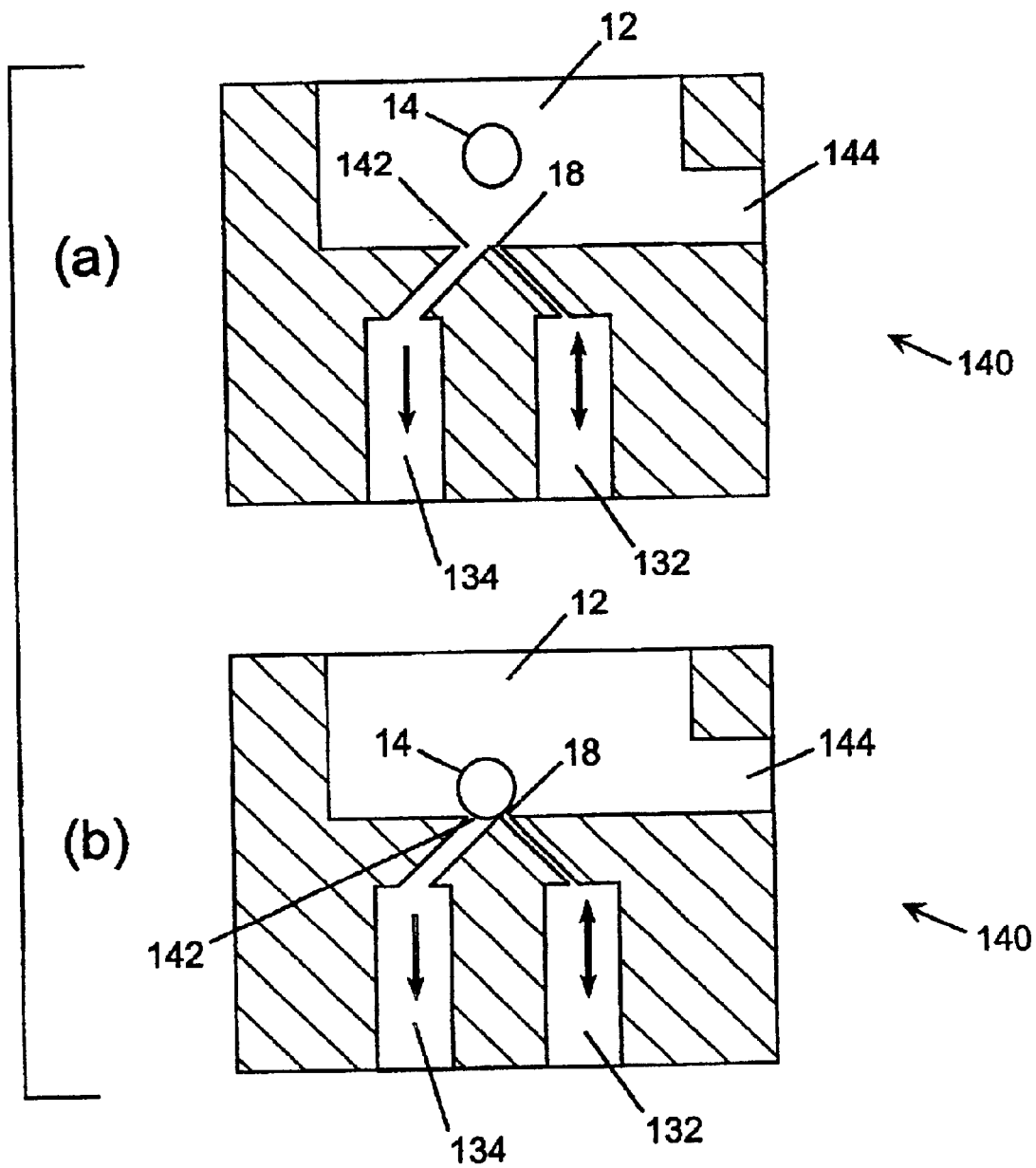
FIG. 18 is a schematic sectional view of a different kind of structure suitable to practice the process of placing a test cell over the electrode aperture according to the invention.

Various changes in the details, steps and components that have been described may be made by those skilled in the art within the principles and scope of the invention herein illustrated and defined in the appended claims. Thus, it is understood that the concept of the invention may be implemented in equivalent fashion with different structural configurations than detailed herein. For example, as illustrated schematically in the perfusion-chamber configuration 140 shown in FIG. 18, the flow of extracellular fluid toward the electrode aperture 18 may be effected by an adjacent aperture 142 subjected to suction through a corresponding extracellular channel 134 (as indicated by the arrow in the figure). An additional outflow port 144 from the extracellular compartment 12 may also be provided to promote the overall flow of extracellular solution within the system. The intracellular channel 132, which serves also as the intracellular compartment of the perfusion chamber, is utilized to apply either positive pressure or suction to the electrode aperture 18 according to the invention, as indicated by the corresponding arrow in the figure.

Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and procedures.

I claim:

1. A method of forming a high-resistance seal between a biological membrane and an electrode aperture in a partition separating an extracellular compartment from an intracellular compartment in a perfusion chamber, comprising the following steps:

delivering an extracellular solution with a biological membrane into said extracellular compartment;

withdrawing the extracellular solution from the extracellular compartment while preventing flow of extracellular solution into the intracellular compartment through the electrode aperture;

directing the extracellular solution and the biological membrane toward the electrode aperture;

monitoring the position of the biological membrane in relation to the electrode aperture; and, as the biological membrane approaches the electrode aperture, inducing fluid flow from the extracellular compartment into the intracellular compartment through the electrode aperture so as to attract the biological membrane to the electrode aperture and produce the formation of a seal between the biological membrane and the electrode aperture;

wherein said step of directing the extracellular solution and the biological membrane toward the electrode aperture is carried out by passing the extracellular solution and the biological membrane through a funnel structure having an opening facing the electrode aperture.

2. The method of claim 1, wherein said step of withdrawing the extracellular solution from the extracellular compartment is carried out by withdrawing the extracellular solution through said opening facing the electrode aperture.

3. The method of claim 2, wherein said step of withdrawing the extracellular solution through said opening facing the electrode aperture is performed by applying suction to the opening.

4. The method of claim 1, wherein said step of directing the extracellular solution and the biological membrane toward the electrode aperture is carried out by passing the extracellular solution through a second aperture adjacent to the electrode aperture.

5. The method of claim 1, wherein said step of inducing fluid flow from the extracellular compartment into the intracellular compartment through the electrode aperture so as to attract the biological membrane to the electrode aperture and to produce the formation of a seal between the biological membrane and the electrode aperture is carried out by applying suction to the intracellular compartment.

6. The method of claim 1, wherein said step of monitoring the position of the biological membrane in relation to the electrode aperture is carried out by sensing a change in electrical resistance across the electrode aperture.

7. The method of claim 1, further including the step of monitoring a direction of fluid flow through the electrode aperture by sensing a change in electrical resistance across the electrode aperture.

8. The method of claim 1, further including the step of providing suction from the intracellular compartment after the formation of said seal between the biological membrane and the electrode aperture to cause a rupture of the biological membrane.

9. The method of claim 8, wherein said suction may be pulsatile.

10. The method of claim 1, wherein said biological membrane includes an animal cell.

11. A method of forming a high-resistance seal between a biological membrane and an electrode aperture in a partition separating an extracellular compartment from an intracellular compartment in a perfusion chamber, comprising the following steps:

delivering an extracellular solution with a biological membrane into said extracellular compartment;

withdrawing the extracellular solution from the extracellular compartment while preventing flow of extracellular solution into the intracellular compartment through the electrode aperture;

monitoring the position of the biological membrane in relation to the electrode aperture; and, as the biological membrane approaches the electrode aperture, inducing fluid flow from the extracellular compartment into the intracellular compartment through the electrode aperture so as to attract the biological membrane to the electrode aperture and produce the formation of a seal between the biological membrane and the electrode apertures;

wherein said step of preventing flow of extracellular solution into the intracellular compartment through the electrode aperture is performed by applying pressure to the intracellular compartment.

12. The method of claim 11, wherein said step of inducing fluid flow from the extracellular compartment into the intracellular compartment through the electrode aperture so as to attract the biological membrane to the electrode aperture and to produce the formation of a seal between the biological membrane and the electrode aperture is carried out by changing said pressure to suction applied to the intracellular compartment.

13. The method of claim 11, wherein said step of monitoring the position of the biological membrane in relation to the electrode aperture is carried out by sensing a change in electrical resistance across the electrode aperture.

14. The method of claim 11, further including the step of monitoring a direction of fluid flow through the electrode aperture by sensing a change in electrical resistance across the electrode aperture.

15. The method of claim 11, further including the step of providing suction from the intracellular compartment after the formation of said seal between the biological membrane and the electrode aperture to cause a rupture of the biological membrane.

16. The method of claim 15, wherein said suction may be pulsatile.

17. The method of claim 11, wherein said biological membrane includes an animal cell.

18. A method of forming a high-resistance seal between a biological membrane and an electrode aperture in a partition separating an extracellular compartment from an intracellular compartment in a perfusion chamber, comprising the following steps:

delivering an extracellular solution with a biological membrane into said extracellular compartment;

withdrawing the extracellular solution from the extracellular compartment while preventing flow of extracellular solution into the intracellular compartment through the electrode aperture;

monitoring the position of the biological membrane in relation to the electrode aperture; and, as the biological membrane approaches the electrode aperture, inducing fluid flow from the extracellular compartment into the intracellular compartment through the electrode aperture so as to attract the biological membrane to the electrode aperture and produce the formation of a seal between the biological membrane and the electrode aperture;

wherein said step of preventing flow of extracellular solution into the intracellular compartment through the electrode aperture is performed by inducing fluid flow from the intracellular compartment into the extracellular compartment through said electrode aperture.

19. The method of claim 18, wherein said step of inducing fluid flow from the extracellular compartment into the intracellular compartment through the electrode aperture so as to attract the biological membrane to the electrode aperture and to produce the formation of a seal between the biological membrane and the electrode aperture is carried out by applying suction to the intracellular compartment.

20. The method of claim 18, wherein said step of monitoring the position of the biological membrane in relation to the electrode aperture is carried out by sensing a change in electrical resistance across the electrode aperture.

21. The method of claim 18, further including the step of monitoring a direction of fluid flow through the electrode aperture by sensing a change in electrical resistance across the electrode aperture.

22. The method of claim 18, further including the step of providing suction from the intracellular compartment after the formation of said seal between the biological membrane and the electrode aperture to cause a rupture of the biological membrane.

23. The method of claim 22, wherein said suction may be pulsatile.

24. The method of claim 18, wherein said biological membrane includes an animal cell.

* * * * *